United States Patent
Fukuchi et al.

(10) Patent No.: US 8,847,166 B2
(45) Date of Patent: Sep. 30, 2014

(54) IMAGING DEVICE USING GAMMA RAYS, IMAGE SIGNAL PROCESSOR, AND IMAGE PROCESSING METHOD FOR GAMMA RAY MEASUREMENT DATA

(75) Inventors: Tomonori Fukuchi, Kobe (JP); Shinji Motomura, Kobe (JP); Shin'ichiro Takeda, Sagamihara (JP); Shuichi Enomoto, Okayama (JP)

(73) Assignee: Riken, Wako-Shi (JP)

( * ) Notice: Subject to any disclaimer, the term of this patent is extended or adjusted under 35 U.S.C. 154(b) by 0 days.

(21) Appl. No.: 13/991,386

(22) PCT Filed: Nov. 15, 2011

(86) PCT No.: PCT/JP2011/076287
§ 371 (c)(1),
(2), (4) Date: Sep. 9, 2013

(87) PCT Pub. No.: WO2012/077468
PCT Pub. Date: Jun. 14, 2012

(65) Prior Publication Data
US 2013/0334429 A1 Dec. 19, 2013

(30) Foreign Application Priority Data
Dec. 9, 2010 (JP) .............................. 2010-274160

(51) Int. Cl.
G06T 7/00 (2006.01)
G01T 1/29 (2006.01)
G01T 1/164 (2006.01)

(52) U.S. Cl.
CPC ............. *G06T 7/0012* (2013.01); *G01T 1/2985* (2013.01); *G01T 1/1642* (2013.01)
USPC .................................... 250/363.03

(58) Field of Classification Search
CPC ...... G01T 1/2985; G01T 1/249; G06T 7/0012
USPC ....................................... 250/363.03
See application file for complete search history.

(56) References Cited

U.S. PATENT DOCUMENTS 6,346,706 B1 * 2/2002 Rogers et al. ............ 250/363.04
6,455,856 B1 * 9/2002 Gagnon ........................ 250/366

(Continued)

FOREIGN PATENT DOCUMENTS

JP 2005208057 A 8/2005
JP 2008232641 A 10/2008

(Continued)

OTHER PUBLICATIONS

Motomura et al., "Gamma-Ray Compton Imaging of Multitracer in Biological Samples Using Strip Germanium Telescope," IEEE Transactions on Nuclear Science 54(3):710-717, Jun. 2007.

(Continued)

*Primary Examiner* — Marcus Taningco
(74) *Attorney, Agent, or Firm* — Seed IP Law Group PLLC

(57) ABSTRACT

To simultaneously image a plurality types of tracer molecules for a Compton image and a PET image. Provided is an imaging device comprising: a first Compton camera (10) for receiving one gamma ray emitted from an imaging target (900) administered by first probe having positron emitting nuclei and second probe having gamma ray emission nuclei; and a second Compton camera (20) which is arranged opposite to the first Compton camera (10) and receives another gamma ray emitted from the imaging target (900). The imaging device is also provided with: an imaging processor for distinguishing and reconstructing a PET image and a Compton image in accordance with the combination of the Compton cameras which detected the gamma rays; and a display for displaying the PET image and the Compton image in association respectively with the first and the second probes.

19 Claims, 14 Drawing Sheets

(56) References Cited

U.S. PATENT DOCUMENTS

| | | |
|---|---|---|
| 8,227,759 B2 | 7/2012 | Fukuchi et al. |
| 2005/0139775 A1 | 6/2005 | Gono et al. |
| 2010/0019156 A1 | 1/2010 | Kohara et al. |
| 2010/0102240 A1 | 4/2010 | Fukuchi et al. |

FOREIGN PATENT DOCUMENTS

| | | | |
|---|---|---|---|
| JP | 2010107312 A | 5/2010 | |
| WO | 2008035708 A1 | 3/2008 | |
| WO | 2008114575 A1 | 9/2008 | |

OTHER PUBLICATIONS

Valk et al., "Positron Emission Tomography," Springer-Verlag London Limited, 2006, pp. 1-16.

International Search Report, mailed Feb. 21, 2012, for PCT/JP2011/076287, 2 pages.

* cited by examiner (a)

(b)

ized, and that image degradation will be prevented accordingly. See Patent Document 1, Paragraph 0013. Patent Document 1 also discloses that, even when directions of a pair of gamma rays form an angle shifted from 180 degrees, a production point of the gamma rays can be estimated, resulting in the improved quantitative performance in images. See Patent Document 1, Paragraph 0013. According to Patent Document 1, the purpose of adopting Compton cameras in PET imaging device is to obtain PET images of high resolution and high quantitative accuracy. See Patent Document 1, Paragraph 0007.

IMAGING DEVICE USING GAMMA RAYS, IMAGE SIGNAL PROCESSOR, AND IMAGE PROCESSING METHOD FOR GAMMA RAY MEASUREMENT DATA

TECHNICAL FIELD

The present invention relates to an imaging device using gamma rays, an image signal processor, and an image processing method of gamma ray measurement data. More specifically, the present invention relates to an imaging device using gamma rays, an image signal processor, and an image processing method of gamma ray measurement data, for detecting both of a gamma ray created by pair annihilation based on radioactive isotope decaying with positron decay and a gamma ray emitted from radioactive isotopes having gamma ray emitting nuclei from an imaging target.

BACKGROUND ART

Recent developments of medical technologies include imaging techniques using tomography on dynamics of tracer molecules in vivo. For example, a positron emission tomography, or PET, has been in practical use (Non-patent Document 1). In PET imaging devices, detection will be made on gamma rays that are emitted through pair annihilation, which is caused by a collision of a positron with an electron in surrounding medium, where the positron is emitted from nuclei of radio isotopes which decay with positron decaying, or positron emitting nuclei. As a result of the pair annihilation two pencils of gamma ray each having energy of 511 keV are emitted into opposite directions, or directions forming substantially 180 degrees angle in between. Generally speaking in PET imaging devices, two or more detectors detect gamma rays in coincidence, and thereafter distributions of the positron emitting nuclei are reconstructed based on the coordinates of detectors that have detected them in coincidence. To be more specific, a medicine to accumulate in cancer cells, is labeled by positron emitting nuclei; the medicine is administered to a living body, or a subject; and the PET imaging device captures in vivo image. This allows imaging of a three-dimensional distribution of cancer cells inside the subject's body, for example.

On the other hand, according to the developments in life science or biomedical science it has been revealed that complex interrelated dynamics among a plurality of molecules is actually underlying activities of living organisms, and moreover, and such dynamics would be related to initiation of lesions.

REFERENCES

Patent Documents

Patent Document 1: JP 2008-232641 A
Patent Document 2: JP 2005-208057 A
Patent Document 3: JP 2010-107312 A

Non-Patent Documents

Non-Patent Document 1: Peter E. Valk et al., "Positron Emission Tomography", ISBN 1-85233-971-3, Springer, (2006)
Non-Patent Document 2: Shinji Motomura et al., "Gamma-Ray Compton Imaging on Multitracer in Biological Samples Using Strip Germanium Telescope", IEEE Trans. Nucl. Sci. Vol. 54, p 710 (2007)

SUMMARY OF THE INVENTION

Technical Problem

A technique for detecting gamma rays produced by pair annihilation in the PET imaging device is disclosed, in which production points of emitted photons, or gamma rays, inside the subject or the imaging target are estimated by using kinematics of Compton scattering (Patent Document 1: JP 2008-232641 A, e.g. Paragraph 0008). Patent Document 1 discloses that, when adopting an arrangement of Compton camera for coincidence detection of a pair of gamma rays of pair annihilation, effects brought by angular fluctuations will be alleviated, and that image degradation will be prevented accordingly. See Patent Document 1, Paragraph 0013. Patent Document 1 also discloses that, even when directions of a pair of gamma rays form an angle shifted from 180 degrees, a production point of the gamma rays can be estimated, resulting in the improved quantitative performance in images. See Patent Document 1, Paragraph 0013. According to Patent Document 1, the purpose of adopting Compton cameras in PET imaging device is to obtain PET images of high resolution and high quantitative accuracy. See Patent Document 1, Paragraph 0007.

However according to the disclosure in Patent Document 1, which only discloses detections of gamma rays caused by pair annihilations, what is imaged is limited to agents or tracer molecules that are labeled by positron emitting nuclei. The agents or tracer molecules may be called a "probe." It follows that, simultaneous imaging that accounts for respective dynamics of a plurality of tracer molecules cannot be performed based only on the disclosure of Patent Document 1. This is because the mechanism disclosed therein for emitting gamma rays toward opposite directions of substantially 180 degrees is responsible only for pair annihilation by the positron emitting nuclei, and as a result it is impossible to make a distinction among the plurality of agents or tracer molecules.

Other approaches of scientific study have been made for simultaneous imaging schemes on the dynamics of a plurality types of tracer molecules, for the purposes of finding functions of living organisms or of finding what initiates the lesions as mentioned above. Such approaches may be referred to as simultaneous imaging on multi nuclei, or simultaneous imaging on multi-tracer. One imaging device regarded as promising for simultaneous imaging on multi-tracer is an image capturing device using Compton cameras. For example, the applicant or the inventors of the present patent application disclosed a gamma ray detector and a gamma ray image capturing device having a Compton camera, which includes multiple electrode planer germanium semiconductor detectors. See Patent Documents 2 and 3, and Non-Patent Document 2.

In capturing images for a simultaneous imaging on multi-tracers by a Compton camera, different types of gamma ray nuclei that emit respective energy gamma rays are used. However according to its operating mechanism in which incoming directions of gamma rays are specified using Compton scattering, it is not always possible to carry out image capturing with sufficient accuracy.

The present invention addresses such problems as stated above. The present invention contributes to further development in diagnostic instruments or in image capturing techniques of molecular imaging in the field of nuclear medicine, by realizing simultaneous multi-tracer imaging that has been desired for finding functions of living organisms, or for finding what initiates the lesions, as well as by improving accuracy of images obtained by Compton scattering detection.

Solution to Problem

The inventors of the present application have conceived of performing imaging on distributions for positron emitting nuclei with high accuracy and imaging using gamma ray emitting nuclei by using a single device. Specifically, a type of a probe having positron emitting nuclei, which is referred to hereinafter as a "first probe," and another type of a probe having gamma ray emitting nuclei, a "second probe," are both administered to an imaging target. Then gamma rays are detected by an imaging device that has a pair of Compton cameras that are oppositely situated each other while placing the imaging target in between. As a result, gamma rays produced by pair annihilation and a gamma ray from the gamma ray emitting nuclei are detectable by the above-mentioned pair of Compton cameras. Furthermore this device enables highly precise differentiation as to which of the first and second probes has created the measurement data or signals for the detected gamma ray. A novel combination in the multi-tracer simultaneous imaging of PET imaging and Compton imaging is provided by reconstructing a PET image and a Compton image based on measurement data or signals with such differentiation, and displaying the reconstructed images respectively in a manner a distinction can be made, by associating the images respectively to accumulation regions of the first and second probes. That is not all. In such an approach, the accuracy of Compton imaging is improved. The present invention is provided on account of these points.

Accordingly, in one aspect of the present invention, provided is an imaging device using gamma rays comprising: a first Compton camera adapted to receive one gamma ray emitted from an imaging target to which a first probe having positron emitting nuclei and a second probe having gamma ray emitting nuclei are administered; a second Compton camera arranged opposite to the first Compton camera and adapted to receive another gamma ray emitted from the imaging target; an imaging processor to perform either a PET image reconstruction or a Compton image reconstruction depending on whether interactions with gamma rays have been detected by the first and the second Compton cameras or interactions with a gamma ray has been detected by either the first or the second Compton camera; and a display for displaying the PET image and the Compton image in association respectively with an accumulation region of the first probe and an accumulation region of the second probe, in a manner distinction can be made from each other.

Typical Compton cameras according to the above aspect of the present invention respectively have a pair of a front gamma ray detector and a rear gamma ray detector. In the above aspect of the present invention, a pair of Compton cameras, each having such pair of gamma ray detectors, are arranged opposite each other for accepting an imaging target in between.

Typical operational mechanisms of these Compton cameras include following two. One mechanism is an operational function as a Compton camera for detecting Compton scattering. In this function, a single pencil of gamma ray from gamma ray emitting nuclei enters first into a front detector. Then Compton scattering takes place in the front detector. At that moment, the gamma ray decreases its energy and changes its direction of travel by an angle, called a scattering angle. In Compton scattering, the photon of the gamma ray loses a part of its energy by recoiling an electron or electrons in the medium of the front detector, with a scattering angle that satisfies conservation laws of energy and momentum. After the Compton scattering the gamma ray that has exited the front detector is detected by the rear detector through photo electronic effect. What is utilized with such a Compton camera is an event that results in absorption of full-energy in the rear detector.

In the above aspect of the present invention, the opposite arrangement of the first and second Compton cameras also makes it possible to detect gamma rays of pair annihilation based on the photo electronic effect in each Compton camera. This is another typical mechanism of function of the Compton cameras in the above aspect. In this case, a straight line that connects points of interactions where the gamma rays have been detected is specified and is used for drawing its trace, or rendering. In addition, measurement signals from the Compton cameras carry signals of interactions based on respective photo electronic effects in the Compton cameras.

As for which of the two typical mechanisms actually worked in detecting a gamma ray, determination can be made based on the measurement signals from the Compton cameras. That is, the imaging processor performs separate operations based on whether interactions with gamma rays have been detected by both of the first and second Compton cameras, or an interaction with a gamma ray has been detected by either of the first or the second Compton camera. The imaging processor operates to reconstruct a PET image when interactions with gamma rays have been detected by both of the Compton cameras and operates to reconstruct a Compton image when an interaction with a gamma ray has been detected by either of the Compton cameras.

It is to be noted that in order to reconstruct the Compton image, the imaging processing for distribution of gamma ray emitting nuclei is performed based on combinations of Compton scattering and absorption thereafter. To accomplish this, kinematics of the Compton scattering are analyzed to determine spatial positions where gamma ray emitting nuclei, which has emitted the gamma rays, may exist, using a conical surface or a surface of a circular cone. Such a cone is specified one for one event, and its generatrixes converging to the apex of the cone represent a set of straight lines, which may represent the direction of travel of the gamma ray before the Compton scattering. This means that specifying one conical surface for each Compton scattering event and depicting overlaps of the surfaces of such cones makes it possible to estimate three-dimensional spatial distribution of the gamma ray emitting nuclei, or distribution of the accumulation region of the second probe having the gamma ray emitting nuclei.

The imaging processor of the imaging device in the above aspect of the present invention is any type of functional means that is able to perform image processing, including any type of functional means implemented in electronic circuitry or a computer. Moreover, the imaging device in the above aspect of the present invention comprises a display for displaying in association respectively with an accumulation region of the first probe and another accumulation region of the second probe, in a manner distinction can be made from each other.

The measurement signals from gamma ray detectors in such structures may be properly utilized in imaging after the signals are processed in a way unique to the gamma ray detectors, for example. Thus, the present invention includes an aspect of an image signal processor.

Accordingly, in another aspect of the present invention, provided is an image signal processor using gamma rays comprising: a first reception channel from a first Compton camera, the first Compton camera being adapted to receive one gamma ray emitted from an imaging target to which a first probe having positron emitting nuclei and a second probe having gamma ray emitting nuclei are administered; a second reception channel from a second Compton camera, the second Compton camera being arranged opposite to the first Compton camera and being adapted to receive another gamma ray emitted from the imaging target; a coincidence finder connected to both the first and the second reception channels, wherein the coincidence finder determines coincidence detection of gamma rays emitted from the imaging target; an imaging processor that performs either a PET image reconstruction or a Compton image reconstruction depending on whether the coincidence finder has determined that interactions with gamma rays were detected by the first and the second Compton cameras or that interactions with a gamma ray were detected by either the first or the second Compton camera; and a display that displays the PET image and the Compton image in association respectively with an accumulation region of the first probe and an accumulation region of the second probe, in a manner distinction can be made from each other.

In the image signal processing device in the above aspect of the present invention, the first and second reception channels are transmission channels to transmit measurement signals or detection signals from the first and second Compton cameras respectively, where the detection signals indicate that gamma rays are emitted from the imaging target. The coincidence finder is implemented by appropriately combining circuit elements of any types, wirings, and processing devices, and is a part that operates to determine based on signals whether the interactions between gamma rays and Compton cameras occurred within a predetermined time period or not.

The present invention is also practiced in another aspect. That is, the present invention may be practiced in a method for processing images to process signals from Compton cameras.

Accordingly, in another aspect of the present invention, provided is an image processing method for gamma ray measurement data, causing a processor in a computer to perform the method, the method comprising steps of: storing measurement data to a storage in a computer, the measurement data obtained by a first Compton camera that is adapted to receive one gamma ray emitted from an imaging target to which a first probe having positron emitting nuclei and a second probe having gamma ray emitting nuclei are administered and obtained by a second Compton camera that is arranged opposite to the first Compton camera and is adapted to receive another gamma ray emitted from the imaging target; coincidence finding for finding coincidence regarding a gamma ray emitted from the imaging target based on the measurement data stored in the storage; imaging processing for performing either PET image reconstruction or Compton image reconstruction depending on whether interactions with gamma rays have been detected by the first and the second Compton cameras or interactions with a gamma ray have been detected by either the first or the second Compton camera; and displaying the PET image and the Compton image in association respectively with an accumulation region of the first probe and an accumulation region of the second probe, in a manner distinction can be made from each other.

In the above-mentioned aspects of the present invention, what are administered to an imaging target are a first probe having positron emitting nuclei and a second probe having gamma ray emitting nuclei. In this combination, positrons are emitted from the positron emitting nuclei due to positron decay, and a pair of gamma ray is produced by pair annihilation of the positron and electron in the surrounding medium. Such gamma rays have energy of 511 keV respectively, and travel into directions having substantially forming 180 degrees angle from each other. In contrast, the gamma ray emitting nuclei directly emits gamma rays. Such gamma rays are ones having energy that depends on the type of nuclei and decay scheme and are emitted by themselves. In the aspects of the present invention, to determine afterward which of the first or the second probe created the detected gamma ray, information as to what type of interaction occurred in either the first or the second Compton cameras is read out from signals of the first and second Compton cameras and utilized.

In the present application, an "event" may denote a phenomenon in which a gamma ray causes interaction with a Compton camera or with a detector in it, such as absorption of gamma ray or energy exchange due to Compton scattering. Also in the present application, the term "coincident" or "coincidence measurement" is not limited to occurrences of two events completely at the same time with infinitesimal tolerance. For example, an actual pair of gamma rays by pair annihilation travels in medium or in space at the speed of light, and is detected each by different detectors through electric charge collection, and separate channels are used for processing the phenomena electrically. Similar processing is used when associating with an identical clock signal by using time stamp data in some aspects of the present invention. Moreover, another similar processing is used for a Compton scattering event in which a single pencil of gamma ray causes Compton scattering and full-energy absorption. That is, complete coincidence in timing cannot be assured, because of various factors in actual situations, including difference in distances between the position of pair annihilation and detectors, difference between Compton scattering detection and full-energy absorption detection, difference in response time of individual detectors, time constants of signal paths used for the transmission, and so on. As such, coincidence in time or coincidence measurement in the present invention does not always denote complete coincidence in timing. Rather, "coincidence" in the concept or in embodiments of the present invention allows a certain amount of difference in timing, or allowable time difference.

In the aspects of the present invention, a computer may be adopted as one of their elements. The computer in such context is generally any sort of computer that has a processor and a recording device, or a memory device, and in which any program operations and resources, such as the recording device, are controlled with the help of an appropriate operating system.

In aspects of the present invention, various sort of recording devices may be adopted, such as the recording device mentioned above, and the first through fourth measurement data storages ("MDSs"). Such a recording device is an arbitrary unit, or a set of units, that is capable of memorizing, or storing information or data, into a memory device in the computer, and is any device that is logically identifiable as necessity. In short, what can be adopted for such a memory device is any type of memory resources that are commonly used for data storing, including any type of computer file, records in databases or its field, and so on. The memory resources are implemented on any types of memory devices commonly used with a computer, such as a main memory, an auxiliary storage, and an external storage. In addition, implemented physical structure for such memory resource is not limited, but rather includes any volatile memory device using a solid state memory device, such as RAM (Random Access Memory), and any non-volatile storage device of a magnetic or semiconductor storage device or the like, such as a hard disc drive or SSD (Solid State Drive)

Advantageous Effect of the Invention

According to some aspects of the present invention, which comprise a pair of Compton cameras arranged opposite each other to receive an imaging target in between, it becomes possible to perform imaging for a plurality types of probes in a manner distinction can be made from each other. In addition, according to some aspects of the present invention, it becomes possible to improve accuracy of images obtained by Compton imaging.

BRIEF DESCRIPTION OF THE DRAWINGS

FIG. 11(a) indicates processing for Compton imaging, and FIG. 11(b) indicates processing for PET imaging.

DESCRIPTION OF THE EMBODIMENT

Figure 1:
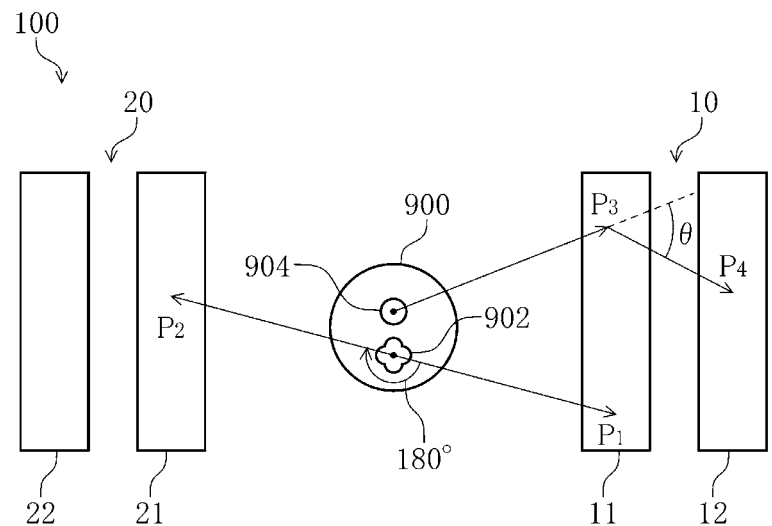
FIG. 1 is a schematic cross sectional view showing a configuration of the first Compton camera and second Compton camera in the structure of the gamma ray imaging device together with gamma rays to be detected in an embodiment of the present invention.

The embodiments of the invention will be described below. For all drawings, the common reference numerals are given to common part or element unless otherwise noted. In addition, each element in the drawing should be understood as not being drawn to scale.

In the description of an embodiment of the present invention, the imaging device using gamma rays as mentioned above will be mainly described throughout Embodiment 1. The image signal processor and the method for image processing for gamma ray measurement data will be mainly described in Sections of signal processing in the imaging device and Sections of the methods concerning the image processing, both of which are also included in Embodiment 1.

Embodiment 1

1. Detectors Configuration

FIG. 1 is a schematic cross sectional view showing a configuration of the first and second Compton cameras in the structure of the gamma ray imaging device 100 together with gamma rays to be detected in the present embodiment. In the gamma ray imaging device 100, the first and second Compton cameras 10 and 20 are arranged opposite each other in a manner they receive imaging target 900 in between. Both of the first and second Compton cameras 10 and 20 have a front detector facing the imaging target 900 and a rear detector disposed behind of respective front detector when viewed from the imaging target. That is, the first Compton camera 10 has first semiconductor detector 11, which is the front detector, and a second semiconductor detector 12, which is the rear detector, as an example. Typically, the first and second semiconductor detectors 11 and 12 are positioned in parallel with a gap in between. The second Compton camera 20 also has a third semiconductor detector 21, which is the front detector, and a fourth semiconductor detector 22, which is the rear detector, to form opposite arrangement with the first Compton camera 10. The third and fourth semiconductor detectors 21 and 22 are also positioned in parallel with a gap in between for example.

In this application, the configuration of the first and second Compton cameras 10 and 20 is presented as they are positioned to the right and to the left of the imaging target 900 as found in FIG. 1. It is to be noted that this configuration of the first and second Compton cameras 10 and 20 is for the explanation purposes only, and it can be changed, in such a way as they are positioned to the above and to the below of the imaging target. In addition, although the description is made with reference to the first and second Compton cameras 10 and 20, the present embodiment is not limited to an example having two Compton cameras. For example the present embodiment may be practiced with three or more Compton cameras to capture images. More specifically, in the example of the present invention, three or more Compton cameras are placed in a ring of a circle, surrounding an imaging target placed near the circle's center, where the Compton camera are placed at equally spaced angles between them and are directed toward the imaging target. In this example of the present embodiment, the same effect and the same function will be realized by selecting a pair of Compton cameras that sit in the arrangement of the first and second Compton cameras described in the above. Moreover, a combination of types of the front and rear detectors that corresponds to each Compton camera is not limited to identical types of detectors. For example, additional semiconductor detectors can be employed to an existing PET imaging device, which have a ring-shaped array of PET detectors, to provide an outer ring-shape array of a number of detectors as a configuration of the detectors of the present embodiment. In such configuration of detectors, a pair of detectors in a radial direction, one is a detector of the existing PET detectors and the other is a detector of additional semiconductor detectors disposed behind when viewed from the imaging target, makes one of the Compton cameras. In this exemplary combination of detectors that are considered to make each Compton camera of the present embodiment, one of the existing PET imaging devices is used for the front detector, and one of the additional semiconductor detectors is used for the rear detector.

1-1. Relationship Between Probes and Captured Images

The imaging target 900 depicted in FIG. 1 is any sort of target whose internal part is to be imaged, such as a part of, or whole of living body of a living creature. In the present embodiment, a type of agent that was labeled by positron emitting nuclei or first probe, and another type of agent that was labeled by gamma ray emitting nuclei or second probe have been administered to the imaging target 900. The first and second probes are typical types of agents that will accumulate specifically to respective living body regions 902 and 904 that develop functions in the living body, where the functions are to be distinguished from each other.

In the present embodiment a type of radiations emitted from the internal part of the imaging target 900 and used for the imaging is a gamma ray. The physical mechanisms for the creation of gamma rays are different for the first probe in the living body region 902 and the second probe in the living body region 904. The gamma rays originated in the first probe are those caused by pair annihilation of a positron emitted from an atomic nucleus of positron emission nucleus through positron decay. That is, gamma rays originating from the first probe are those created by the pair annihilation due to the positron from the positron emission nucleus and an electron of the surrounding medium. Such gamma rays are a pair of energy quanta, or photons, each having a specific energy (511 keV, or $81.9 \times 10^{-15}$ Joule), which corresponds to mass of the positron and electron. The pair of gamma rays is emitted at a position of the pair annihilation, or each part of the accumulated first probe in the living body region 902 and travels to opposite directions of substantially 180 degrees from each other. In contrast, gamma ray emitting nuclei of the second probe directly emit a gamma ray, by a form of a single photon having respective energy depending on the types of nuclei. The mechanism for generating this gamma ray is nuclear decay, as an example. Such a gamma ray is emitted from the second probe that is accumulating each part of the living body region 904.

The inventors of the present application have paid attention to the fact that imaging may be performed for both of the first and second probes by the first and second Compton cameras 10 and 20. By combining detectors included in the first and second Compton cameras 10 and 20 mentioned above, both of the pair annihilation 511 keV gamma rays in a pair are detectable, allowing us to locate where each gamma ray interacted with the detectors. As such, the distribution image of the first probe can be captured. Moreover, capturing the distribution image of the second probe is possible without changing the Compton cameras' configuration. This is because each Compton camera has measurement capability of Compton scattering. In the present application, PET imaging may denote a sequence of processing steps for imaging that use a nature of opposite travels, or substantial 180 degree opposite emissions, of gamma rays due to pair annihilation. Likewise, in the present application, Compton imaging may denote a sequence of processing steps in which gamma rays are detected using Compton scattering and imaging is performed therefrom. In addition, the terms of PET image and Compton image are also used for denoting respective images or image data that are captured by PET imaging and Compton imaging respectively.

1-2. Structure of Detectors

Figure 2:
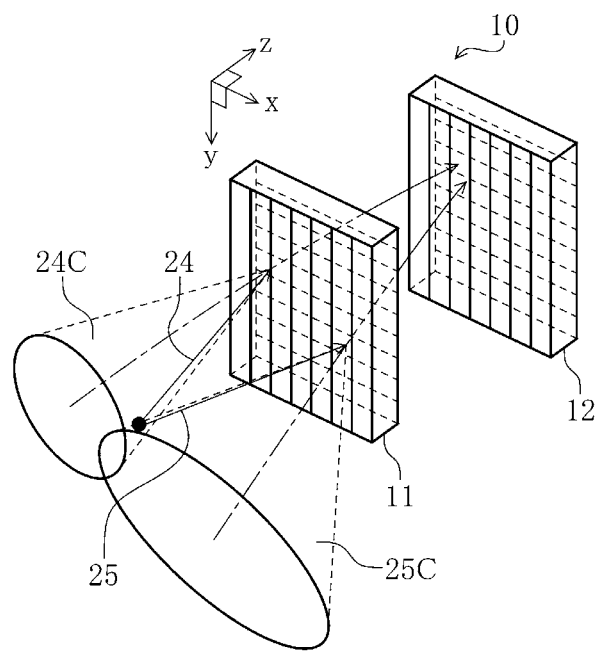
FIG. 2 is a perspective view of the first Compton camera having the first and second semiconductor detectors in an embodiment of the present invention.

In the present embodiment, the semiconductor detectors or the first-fourth semiconductor detectors 11-22 are typically multiple electrode planer semiconductor detectors. FIG. 2 is a perspective view of the first Compton camera 10 in the present embodiment having the first and second semiconductor detectors 11 and 12, each of which is a multiple electrode semiconductor detector. The Compton camera 20 also has the same structure as the first Compton camera 10. That is, the second Compton camera 20 has third and fourth semiconductor detectors 21 and 22, and is arranged opposite to the first Compton camera 10 for accepting the imaging target 900 (not shown in FIG. 2) between the first and second Compton cameras 10 and 20.

In each semiconductor detector in the first and second Compton cameras 10 and 20, a set of strip electrodes are formed on both surfaces that forms a thickness of a high pure germanium plate, or planer detector. The strip electrodes are aligned to form stripe patterns on both surfaces, and directions of the stripes between the both surfaces are crossing each other. In the first and second semiconductor detectors 11 and 12 in the first Compton camera 10 in FIG. 2, each strip electrode is extending along y direction and are aligned in x direction on a surface that faces the imaging target 900, which is hereinafter referred to as the "front surface," of the plate of germanium. On the other hand, each strip electrode extending along x direction is aligned in y direction on the other surface, or "rear surface." Strip electrodes are electrically isolated from adjacent strip electrodes on the same surface by providing narrow spacing between them. Each set of strip electrodes on the surfaces has respective predetermined number of the strip electrodes. In this example, we assume each set has thirteen electrodes as in the actual Compton camera we built; however it is merely an example for explanation purposes. Also, note that FIG. 2 does not indicate all strip electrodes.

In the first-fourth semiconductor detectors 11-22, the plate of semiconductor has an $n^+$ semiconductor layer at its outmost layer in the front surface side, a p semiconductor layer at its outmost layer in the rear surface side, and an intrinsic semiconductor layer filling between the $n^+$ and p semiconductor layers. When making a measurement, each semiconductor detector is cooled for example to liquid nitrogen temperature (−196 degree-C., or 77K) if they are made of germanium. As a result, each semiconductor plate in the first-fourth semiconductor detectors works like intrinsic semiconductors with suppressed thermal excitations of conduction carriers. However, the semiconductor detectors adopted in the present embodiment are not limited to those that require cooling for detection operation. Detectors for practicing the embodiment of the present invention include semiconductor detectors that can perform detection without cooling. In addition, what can be used for practicing the embodiment of the present invention are any types of semiconductor detectors that do not require cooling but work with cooling preferably in that they may well show better accuracy. When the detectors are cooled, each semiconductor detector is placed inside of a cryostat and cooled by appropriate coolant or by a refrigerator through good thermal conductor, such as copper blocks.

Through each strip electrode on both surfaces of each semiconductor plate in the first-fourth semiconductor detectors 11-22, a reverse bias voltage of around 1-5 kV is applied between both sides to produce electric field of thickness direction in the semiconductor plate. As a result, when a gamma ray enters into the semiconductor plate of each semiconductor detectors, the gamma ray and electrons in the semiconductor may interact with each other in the intrinsic semiconductor region. The electrons receive transferred energy from the gamma ray. Then a number of carrier charges are created along the pass of the energized electrons, and the created carrier charges are drifted and collected according to the reverse bias voltage. Note that the electric current caused by the carrier charges reflects the energy of electrons that interacted with the gamma ray. Thus, when full-energy absorption occurs with the gamma ray, photo electronic effect takes place; the carrier charges are generated along the pass of the electrons; and the electric current that corresponds to the full-energy of the gamma ray is detected. In contrast, when Compton scattering occurred for a gamma ray, the interaction mentioned above is caused by the Compton scattering; and along the pass of electrons recoiled by the gamma ray, or recoil electrons, carrier charges are also created and the electric current reflecting the loss of energy of the gamma ray is detected. It should also be noted that the interactions between the gamma ray and electrons occurs substantially at a single point, whichever they are caused by full-energy absorption or by Compton scattering. That is, the passing ranges of electrons are within around 1 mm, though they may depend upon the energy received by the electrons.

In the present embodiment, the other type of medium than germanium plate in the above may be selected for the first-fourth semiconductor detectors. The material for the medium of each semiconductor detector of the present embodiment is not limited as long as the material has sensitivity to gamma rays. In addition to germanium, examples of the semiconductor part of the first-the fourth semiconductor detector include silicon, cadmium telluride, cadmium zinc telluride, and diamond.

1-3. Imaging Principle: PET Imaging

In the present embodiment, the principles of measurement and imaging for PET imaging which uses the first and second Compton cameras 10 and 20 are as follows. First, as illustrated in FIG. 1, gamma rays of pair annihilation are emitted to opposite directions of substantially 180 degrees. One of the gamma rays is detected by either of the first or second semiconductor detector 11 or 12 of the first Compton camera 10 for example. The other of the gamma rays is detected by either of the third or fourth semiconductor detector 21 or 22 of the second Compton camera 20. When such combination of detectors detects events in coincidence, detected pair of gamma rays may be possibly generated by pair annihilation. Therefore, one straight line connecting detection points, one by the gamma ray in the first Compton camera 10, and another by the other gamma ray in the second Compton camera 20, is determined for each set of such coincident events.

After such events are detected several times and a plurality of straight lines are determined, a spatial position where more number of straight lines overlaps is considered as a position where more number of gamma rays are generated by pair annihilation in the agent labeled by the positron emitting nuclei, or the first probe. That is, the living body region 902, which corresponds to a distribution of the first probe, is reproduced as the overlap of the plurality of straight lines. Also, the radioactivity of positions for the first probe, or the accumulation, is represented by the amount of the overlaps of the straight lines, or multiplicity, at every spatial point. Thus obtained accumulation of the first probe at every spatial point is recorded by rendering determined straight lines for the spatial points. More specifically, memory values corresponding to each of the straight lines in voxel values representing the space are changed and recorded in a usual manner, such as counting up, for recording the accumulation of the first probe at every spatial point. By retrieving such memory values for each voxels from the recorded storages after the image capturing, an image showing radioactivity of the first probe at every spatial point in grayscale will be reconstructed. This is the principle of the PET imaging of the present embodiment. In addition to the determination by the combination of detectors mentioned above, checking whether the energy is 511 keV or not may be optionally adopted for reducing erroneous results in the determination.

The PET imaging of the present embodiment differs from one in conventional PET imaging devices, in that a process for specifying detection points of gamma ray, or interaction points, is performed in a multiple electrode planer germanium semiconductor detector. By distinguishing signals created by respective strip electrodes during the processing, interaction points in semiconductor electrodes are specified as points on a plane of the semiconductor plate. However, only from the perspective that interaction points of gamma rays are derived for capturing the images, the above operation is identical to the general PET imaging.

1-4. Imaging Principle: Compton Imaging

The imaging principle for imaging of gamma ray emitting nuclei by Compton scattering with the first and second Compton cameras 10 and 20 in the present embodiment is almost the same as one for conventional Compton camera. That is, when a gamma ray enters the first Compton camera 10 indicated in FIGS. 1 and 2, Compton scattering takes place with a certain probability in the first semiconductor detector 11; and the scattered gamma ray then enters the second semiconductor detector 12. To determine whether the detected signal is of Compton scattering or not, the timings of detected signal waves measured in the first and second semiconductor detectors 11 and 12 and energy values detected in the first and second semiconductor detector 11 and 12 are used. If it is highly likely that the detected event was caused by Compton scattering, the scattering angle is determined based on kinematics of Compton scattering for the energy, and one conical surface determined for each event. Specifically, the gamma ray's direction of travel after the Compton scattering is given by a straight line connecting detection points in the front and rear detectors. The scattering angle is determined by a formula for kinematics of Compton scattering for the energy values of the gamma ray, where the energy values are of total energy and is energy of the gamma ray at the time of emission, and of energy measured in the rear detector for the same gamma ray. Thus, one conical surface is determined for each event in combination of the results. That is, the cone has the straight line of the gamma ray's direction of travel after the Compton scattering as its axis, the detection point, or the interaction point, in the front detector as its apex, and the scattering angle as its half-angle at the apex.

The process mentioned above will be more easily understood with reference to FIG. 2. For example, the conical surface 24C is determined for the gamma ray 24, and the conical surface 25C is also determined for the gamma ray 25 for another event, as indicated in FIG. 2. Likewise, additional conical surface will be added each for subsequent events, though not indicated in FIG. 2. Therefore more number of such conical surfaces overlap where more gamma rays are created from the gamma ray emitting nuclei. That is, the distribution of second probe, or the living body region 904, is depicted as spatial positions where more number of such conical surfaces overlap; thus radioactivity of positions for the second probe, or accumulation, corresponds to the amount of the overlapping, or multiplicity, of the conical surfaces at every spatial point. Also note that every determined cone is recorded by associating it to spatial points. In so doing, the fact that each voxel laying on each conical surface will be recorded by changing memory values for voxels that correspond to the conical surface. By retrieving such memory values of addresses corresponding to the voxels from the recorded storage after image capturing, an image showing radioactivity of the second probe at every voxel will be reconstructed in grayscale. The imaging principle for the gamma ray emitting nuclei is identical to those of conventional imaging with Compton camera.

In the present embodiment, what should be distinct from the conventional imaging of Compton camera is, first, that all conical surfaces obtained from both the first and second Compton cameras 10 and 20 contribute to determination of distribution of the second probe in this embodiment. However, note that the Compton imaging of the present embodiment does not always require both of the first and second Compton cameras 10 and 20. Second, the present embodiment uses a combination of PET imaging and the Compton imaging mentioned above to implement imaging of spatial distributions of the first and second probes. Moreover, a problem that may be caused in Compton imaging would be overcome, which will be described later in "4. Improving Accuracy".

2. Principle for Differentiating PET Imaging and Compton Imaging

Figure 3:
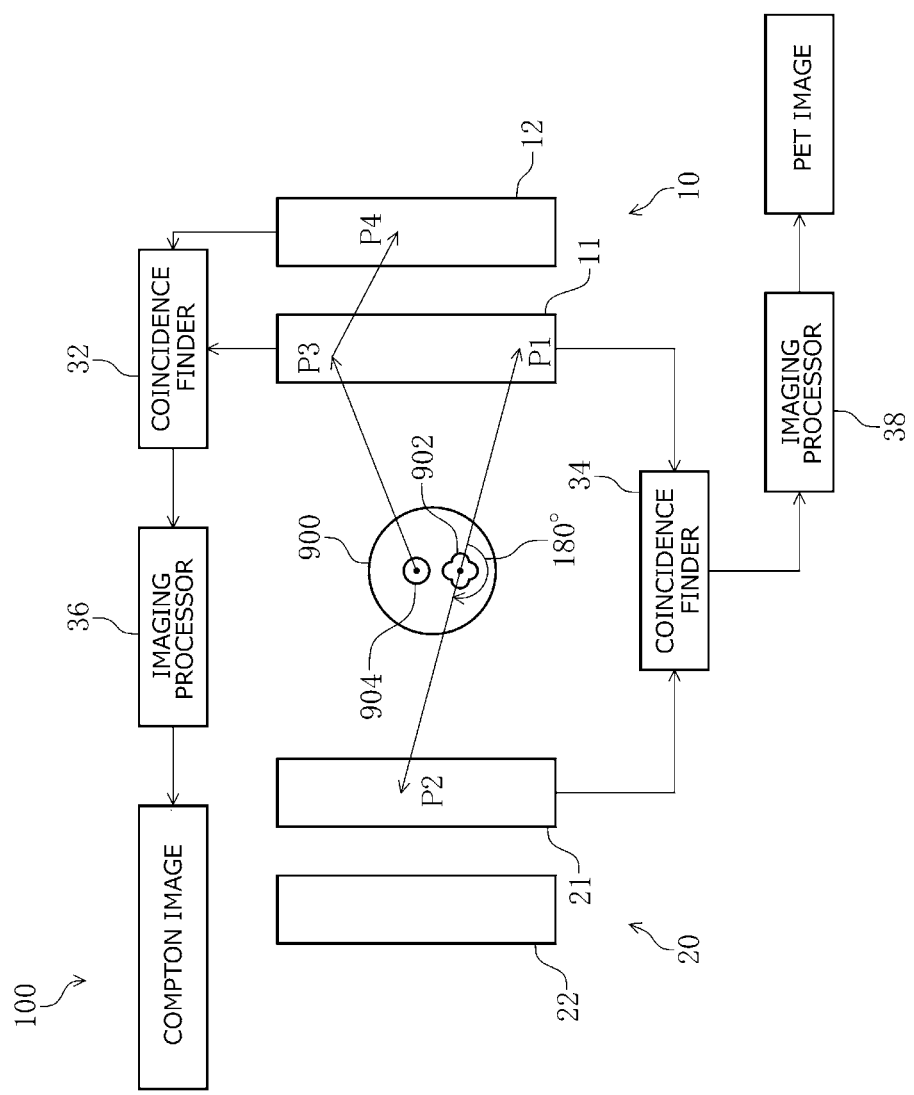
FIG. 3 is a schematic block diagram illustrating each functional means in a processing system performing PET imaging and Compton imaging in a most simplified depiction in an embodiment of the present invention.

In the gamma ray imaging device 100 of the present embodiment, gamma rays are used for imaging while differentiating PET imaging and Compton imaging from each other. Controlling as to which of these imaging processing should be performed in the present embodiment may be implemented in forms of signal processing and of data processing. FIG. 3 is a schematic block diagram illustrating each functional means in a processing system performing PET imaging and Compton imaging in the present embodiment of the present invention in a most simplified depiction. FIG. 1 depicts an operation for a principle that is common to both forms of embodiment, signal processing form and data processing form, as well as the configuration of the detectors.

FIG. 3 indicates that the measurement signals from the first and second semiconductor detectors 11 and 12 among the first-fourth semiconductor detectors 11-22 are input to coincidence finder 32, and that output from the coincidence finder 32 is used for image processing by imaging processor 36 to obtain Compton images. The coincidence finder 32 operates to extract, from measurement signals by the first and second semiconductor detectors 11 and 12, measurement signals corresponding to events occurred in coincidence at the first and second semiconductor detectors 11 and 12. In the present embodiment, measurement signals that have been output in response to events from semiconductor detectors may also be referred to as detection signals. If Compton scattering in the first semiconductor detector 11 and full-energy absorption in the second semiconductor detector 12 occurred in coincidence, then detection signals are extracted by the coincidence finder 32. The detection signals in such a case are used for image processing by the imaging processor 36 to generate Compton images. Likewise, coincidence finder 34 operates to extract, from measurement signals by the first and third semiconductor detectors 11 and 21, measurement signals corresponding to events occurred in coincidence in the first and third semiconductor detectors 12 and 21, or detection signals. When gamma rays are absorbed in coincidence in the first and third semiconductor detectors 11 and 21, the detection signals are extracted by the coincidence finder 34. The detection signals in such a case are used for image processing by the imaging processor 38 to generate PET images.

As described in the above, the imaging processing in the present embodiment in FIG. 3, or the functional means for imaging processors, is practiced in two embodiment forms. One is a form of signal processing in electronic circuitry to extract detection signals corresponding to events from measurement signals. This form will be described below in "2-1. Differentiating Operations through Signal Processing". The other is a form of information processing in a computer after measurement signals are acquired and transferred through a signal processor with minimal dead time to the computer, for processing with differentiation between Compton imaging and PET imaging. Such form of embodiment will be described later in "2-2. Differentiating Operations through Data Processing". In both embodiment forms, patterns of combinations of semiconductor detectors actually detected gamma rays, or referred to as "hit pattern", are used to differentiate operations in the process.

2-1. Differentiating Operations Through Signal Processing

Figure 4:
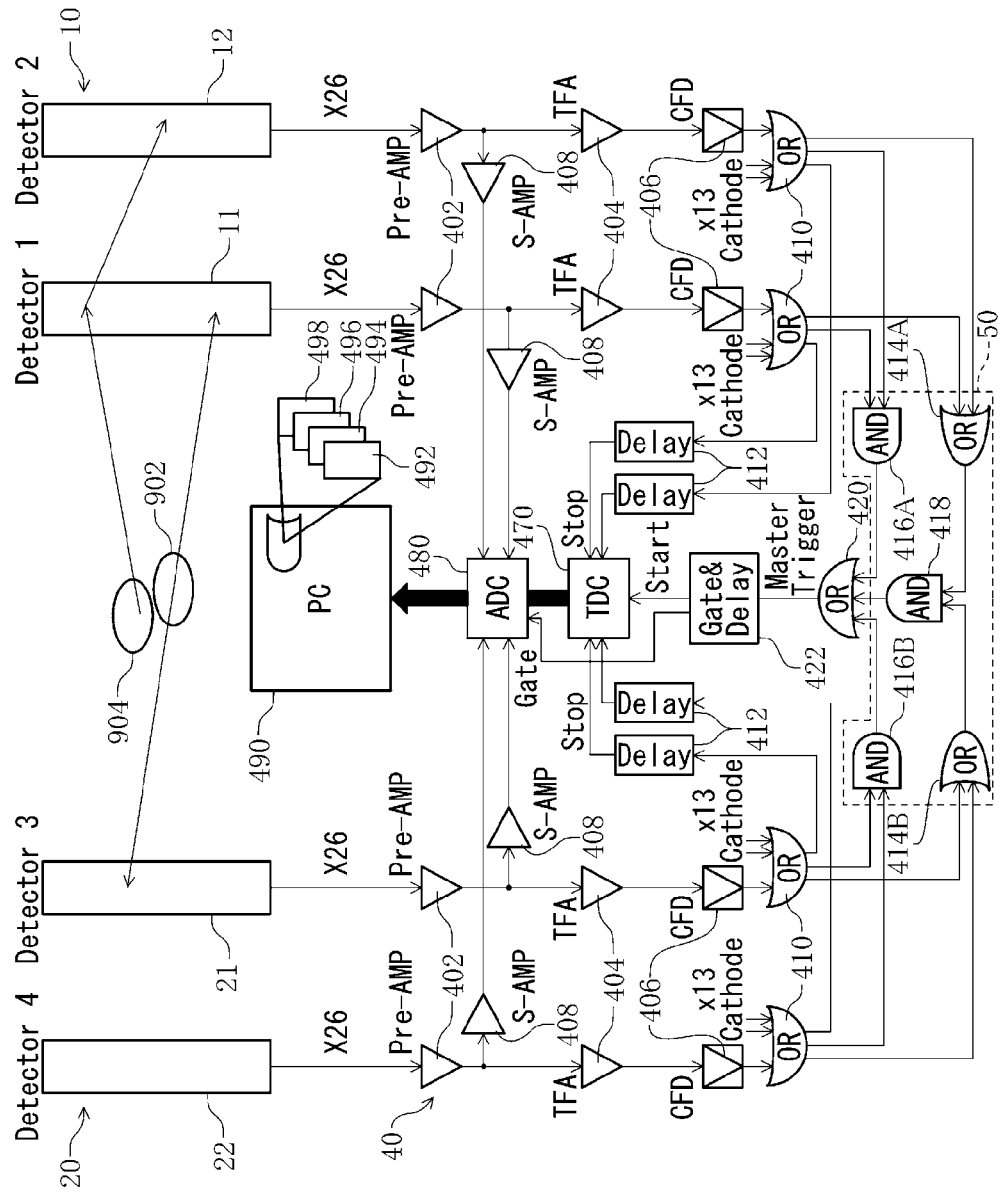
FIG. 4 is a circuit diagram showing an example of the circuit structure for realizing functional means as depicted in FIG. 3 in an embodiment of the present invention.

FIG. 4 is a circuit diagram showing an example of circuit structure 40 realizing functional means as depicted in FIG. 3. The circuit structure 40 is one form of the present embodiment in which image processing in the gamma ray imaging device 100 is implemented. Fifty two signal paths are connected as first reception channel to the first Compton camera 10. Also note that the first reception channel operates to transmit signals from the first and second semiconductor detectors 11 and 12. Likewise, fifty two signal paths are connected as second reception channel to the second Compton camera 20. The second reception channel operates to transmit signals from the third and fourth semiconductor detectors 21 and 22. That is, each of the first-fourth semiconductor detectors 11-22 has thirteen strip electrodes on the front and rear surfaces of itself as illustrated with the first and second semiconductor detectors 11 and 12 in FIG. 2, making total of twenty six measurement signal channels for each semiconductor detector. In the present embodiment, measurement signals for each of the first-fourth semiconductor detectors 11-22 are referred to as the first-fourth measurement signal channels. Also, two times of them, or fifty two signal paths are connected to each Compton camera. The first or second reception channel, each having fifty two reception channels for transmitting measurement signals respectively from the front and rear semiconductor detectors, are connected to the first or the second Compton camera. In FIG. 4, twenty six signal paths from each semiconductor detector are indicated. Thus, the first reception channel from the first Compton camera 10 includes the first measurement signal channels from the first semiconductor detector 11 and the second measurement signal channels from the second semiconductor detector 12. Likewise, the first reception channel from the second Compton camera 20 includes the third measurement signal channels from third semiconductor detector 21 and the fourth measurement signal channels from the fourth semiconductor detector 22.

In the circuit structure 40, all output signal lines from the pre-amplifier (Pre-AMP) 402 are divided into two groups:

one includes signal paths for timing, and the other includes signal paths for amplitude. The signal paths for timing are connected to constant fraction discriminator (CFD) 406 via timing filtering amplifier (TFA) 404. On the other hand, the signal paths for amplitude are connected to analog-to-digital converter (ADC) 480 via shaping amplifier (S-AMP) 408.

The TFA 404 is a circuit used for shaping pulses and improving signal-to-noise ratio, or S/N ratio, for timing measurement. From CFDs 406, only thirteen lines of electrodes on the front side, which act as cathodes, are transmitted next to OR gates 410. This is because coincidence and hit pattern are both detected from the cathodes' outputs. The output from the CFD 406 is a trigger signal independent of the amplitude, or the pulse height, in response to the rising in the input to CFD 406. When at least one of signals in outputs of thirteen CFDs 406 is asserted, the outputs of OR gate 410, each of which has three outputs are also asserted. An output from the three outputs of each OR gate 410 is input to delay circuit 412. The circuitry of such a structure is connected the first-fourth semiconductor detectors 11-22.

The two outputs from the OR gate 410 in the circuit structure 40 are input to OR gate 414A or 414B and the AND gate 416A or 416B, together with outputs from the OR gate 410 from semiconductor detectors that is a counterpart of each pair of semiconductor detectors for the first and second Compton cameras 10 and 20. For example, one output is provided from each OR gate 410 corresponding to the first and second semiconductor detectors 11 and 12 to the OR gate 414A and AND gate 416A related to the first Compton camera 10 found in the right half of FIG. 4. The output of the OR gate 414A is input to AND gate 418 together with an output of the OR gate 414B related to the second Compton camera 20. On the other hand, the output of the AND gate 416A is input to the OR gate 420 together with the output of AND gate 416B and the output of AND gate 418, where the AND gate 416B is related to the second Compton camera 20. The output of OR gate 420 becomes a start signal for time-to-digital converter (TDC) 470 and a gate signal to ADC 480.

Figure 5:
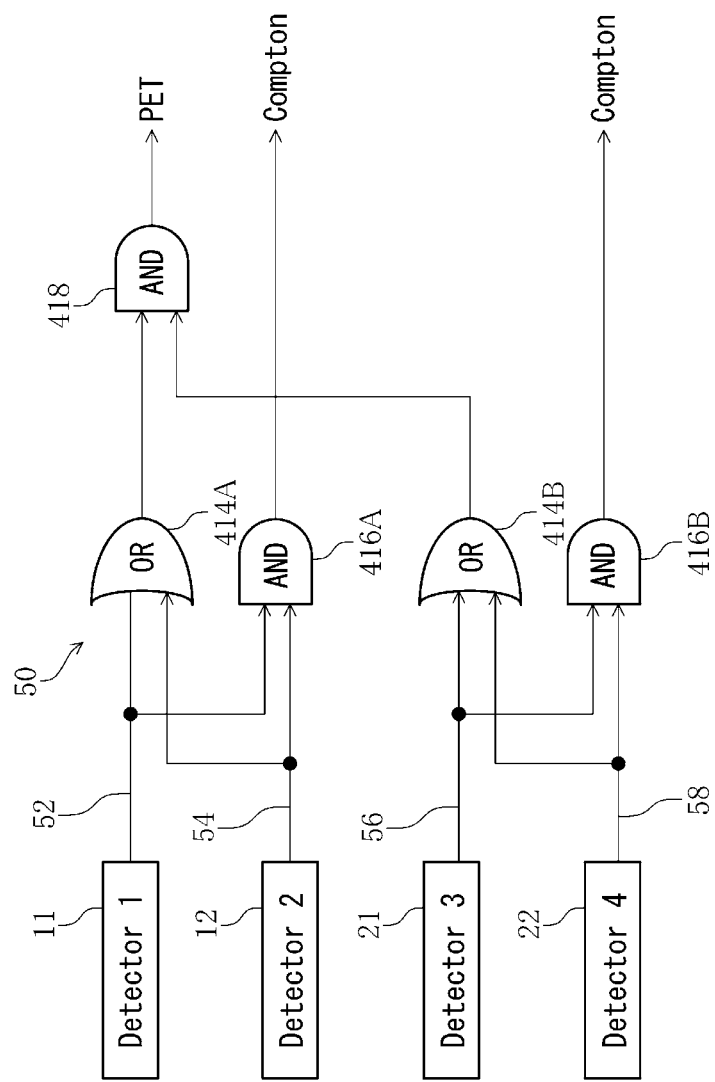
FIG. 5 is a circuit diagram showing only logical elements or a part relating to functional means in FIG. 3 out of FIG. 4 in an embodiment of the present invention.

FIG. 5 is a circuit diagram showing elements of circuitry out of signal paths for timing in the circuit in FIG. 4, or parts relating to coincidence measurement finder 50 that operates as functional means for coincidence detection and hit pattern in FIG. 3. The logic circuit ranging from the OR gate 410, which receives from each semiconductor detectors, to the OR gate 420 in FIG. 4 is expressed as one measurement signal channel each from the first-fourth semiconductor detectors 11-22 to the OR gate 414A or 414B, or the AND gate 416A or 416B. These measurement signal channels are referred to as first, second, third, and fourth measurement signal channels 52, 54, 56, and 58 respectively. Of these, the first and the second measurement signal channels 52 and 54 belong to the first reception channel stated above, whereas the third and the fourth measurement signal channels 56 and 58 belong to the second reception channel.

A case in which gamma rays detected in the coincidence measurement finder 50 in FIGS. 4 and 5 are treated for PET imaging is when the AND gate 418 is asserted. That is, if a detection signal of an event is output from either of the first and second semiconductor detectors 11 and 12 and, at the same time, another detection signal of another event is output from either of the third and fourth semiconductor detectors 21 and 22, then PET imaging is processed. Therefore, the first and second measurement signal channels 52 and 54, which are asserted or negated in response to each measurement signal from the first and second semiconductor detectors 11 and 12, are connected as inputs to the OR gate 414A. Likewise, the third and fourth measurement signal channels 56 and 58, which are asserted or negated in response to each measurement signal from the third and fourth semiconductor detectors 21 and 22, are connected as inputs to the OR gate 414B. The two outputs from the OR gates 414A and 414B are input to the AND gate 418. The output signal from the AND gate 418 is used as a PET determination signal.

In contrast, a case in which gamma rays detected in the coincidence measurement finder 50 are treated for Compton imaging is when detection signals are output from both of the first and second semiconductor detectors 11 and 12, or when detection signals are output from both of the third and fourth semiconductor detectors 21 and 22. Therefore, paths from both measurement signals of the first and second semiconductor detectors 11 and 12, or the first and second measurement signal channels 52 and 54, are input to the AND gate 416A. Likewise, outputs from both of the third and fourth semiconductor detectors 21 and 22, or the third and fourth measurement signal channels 56 and 58, are input to the AND gate 416B. Outputs from the AND gates 416A and 416B are asserted when the Compton scattering is detected in the first and second Compton cameras 10 and 20 respectively. Simply put, the output signals from the AND gates 416A and 416B are used as a Compton scattering determination signal, which is asserted for performing Compton image processing using signals from the Compton cameras.

As stated above, the coincidence measurement finder 50 in FIGS. 4 and 5 realizes functions for determining coincidence and hit pattern by using the group of gates and wiring included therein.

Referring back to FIG. 4, the rest of the circuit elements in the circuit structure 40 is now described. The output of OR the gate 420, or a master trigger signal, is asserted when detection signals are found to be coincident. The master trigger signal from the OR gate 420 is adjusted in Gate&Delay 422 to be used as a start signal for the TDC 470. The output from the delay circuit 412 is used as the stop signal for the TDC 470. The Gate&Delay 422 issues a start signal toward the TDC 470 and outputs a gate signal toward ADC 480 disposed in the signal path for amplitude. The TDC 470 records the time difference between the start and stop signals. In addition, the ADC 480 is a circuit element that converts analog values of the amplitude signal from the S-AMP 408 to digital ones and records the pulse shape, or maximum value in the output signal from the S-AMP 408 while the gate signal is output from the Gate&Delay 422. The S-AMP 408 shapes and amplifies its input waveform to have a waveform that can be easily processed later for better accuracy. Lastly, recorded data are transferred to the computer 490 by the TDC 470 and the ADC 480.

In the computer 490 in FIG. 4, data from the first-fourth semiconductor detectors 11-22 are recorded in first-fourth event data storages 492, 494, 496, and 498 respectively. The circuit structure 40 in FIGS. 4 and 5 is an example of circuits that embody functional means for detecting coincidence as well as the hit pattern. The present embodiment may include other circuit structure that implements similar functions for realizing functional means for detecting the coincidence and the hit pattern.

2-2. Differentiating Operations Through Data Processing

The gamma ray imaging device 100 of the present embodiment may be implemented differently from the circuit structure 40 in FIG. 4. For example, the present embodiment may be implemented in such a manner that the outputs from the semiconductor detectors are associated respectively with time information, or time stamp, and stored as continuous or sequential measurement data, and then the coincidence determination is made on such stored measurement data. In this case, by adopting data obtained from the gamma ray imaging device 100 of the present embodiment, it is possible to determine which processing of PET imaging or Compton imaging should be performed.

Figure 6:
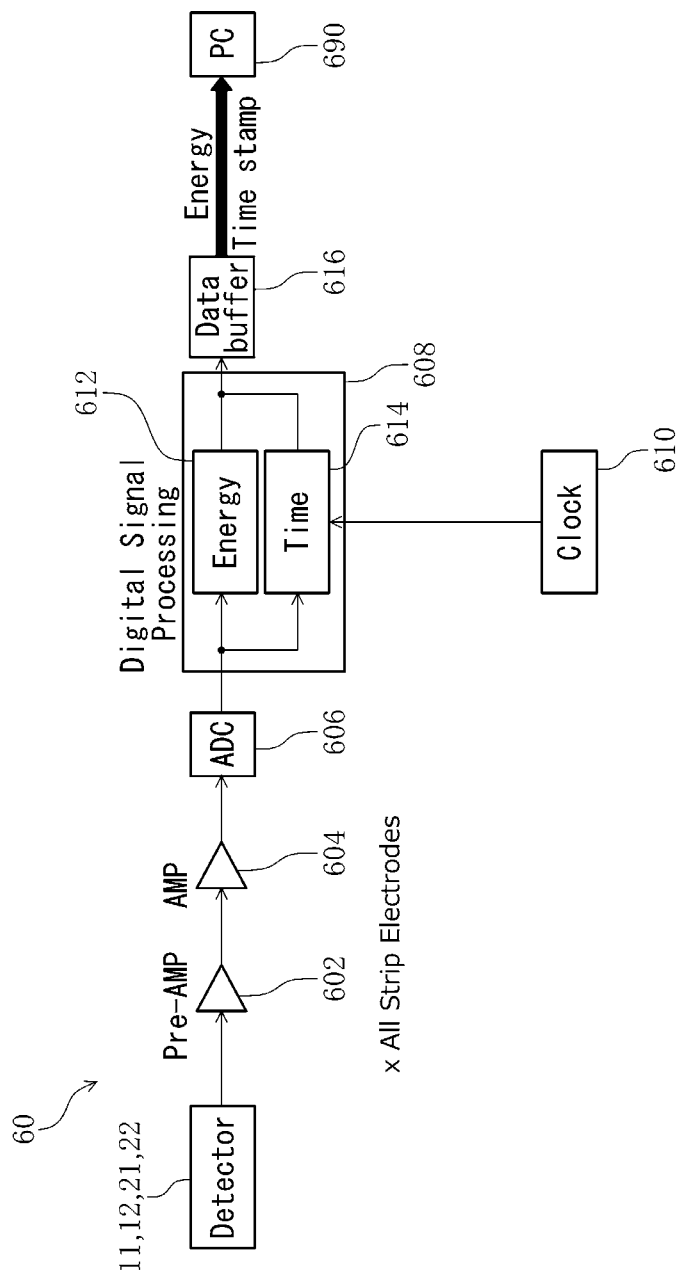
FIG. 6 is a block diagram showing the circuit structure of reception channels that are used for coincidence determination by data processing in an embodiment of the present invention.

FIG. 6 is a block diagram showing the circuit structure of measurement signal channels 60 that are used for coincidence determination based on data processing. The circuit in FIG. 6 is the measurement signal channels 60 ranging from each of the strip electrodes in the first-fourth semiconductor detectors 11-22 to the computer 690. The measurement signal from each electrode in the semiconductor detector is amplified in pre-amplifier 602 and input to another amplifier (AMP) 604. The AMP 604 is used to adjust the dynamic range. The output from the AMP 604 is then input to analog-to-digital converter (ADC) 606. The signals from each electrodes of the semiconductor detector to the ADC 606 are analog, and, if the gamma ray is detected, the waveforms in signal paths reflect energies accompanying the interactions of a gamma ray. Such analogue waveforms are converted to digital signals by the ADC 606. The digital signals are signals of digital data of the waveforms sampled and quantized by a predetermined sampling rate and a predetermined bit depth. The sampling rate is set to 100 MHz for example, and the quantization bit depth is set to 8 to 16 bits for example and typically to 14 bits. For the purpose of achieving better accuracy, higher rate sampling and larger bit depth quantization are ideal. However, the greater the sampling rate, the more amount of noise is generated in the actual ADC. Therefore, typically the conditions mentioned above are adopted, considering the balance between accuracy in the digital expression and the noise.

The digital data signal of the waveform is input to the digital signal processor (DSP) 608. Two processes are performed in the DSP 608 in general. One process is to extract gamma ray energy information from the digital data signal for the waveform. The other process is to add time stamp to the energy information. Such processes are schematically illustrated in FIG. 6. The digital signal of output from the DSP 608, or digital measurement signal, includes energy field 612 and time field 614. The energy field 612 includes as digital data energy values extracted from digital waveform data signal in the input. On the other hand, the time field 614 includes time data from clock generator 610 that gives time stamp information. By using the time field 614 in digital measurement signal of each signal path, hereinafter called "digital measurement signal unique to signal path," or "DMSUSP," the time when each value in the energy field 612 was obtained can be specified. The DMSUSP is temporarily stored in data buffer 616 as data values, and transferred to the computer 690 at an appropriate timing. The data value is referred to as "measurement data unique to signal path," or "MDUSP." As a matter of convenience of the description, the MDUSP is also assumed to have the energy field 612 and the time field 614.

It is to be noted, on one hand, that the measurement signal channel 60 is provided for each strip electrode of each semiconductor detector, on the other hand, that the clock generator 610 and the computer 690 are common to all strip electrode for all semiconductor detectors. For this purpose the time field 614 retains time stamp data that represents counts by the clock generator 610 provided in common. That is, by resetting the clock generator 610 at the time of stating the measurement, it is possible to give elapsed time from the start as time information common to all signal paths. In addition, the DSP 608 executes in pipeline operation and each measurement signal channel 60 are processed concurrently. For this purpose, the circuit structure of the measurement signal channels 60 in FIG. 6 are made to have minimal dead time. After transferred to the computer 690, the MDUSP is stored in the first-fourth MDSs 722-728 (FIG. 7) in the computer 690 associated respectively with a combination of the semiconductor detector and strip electrode.

Figure 7:
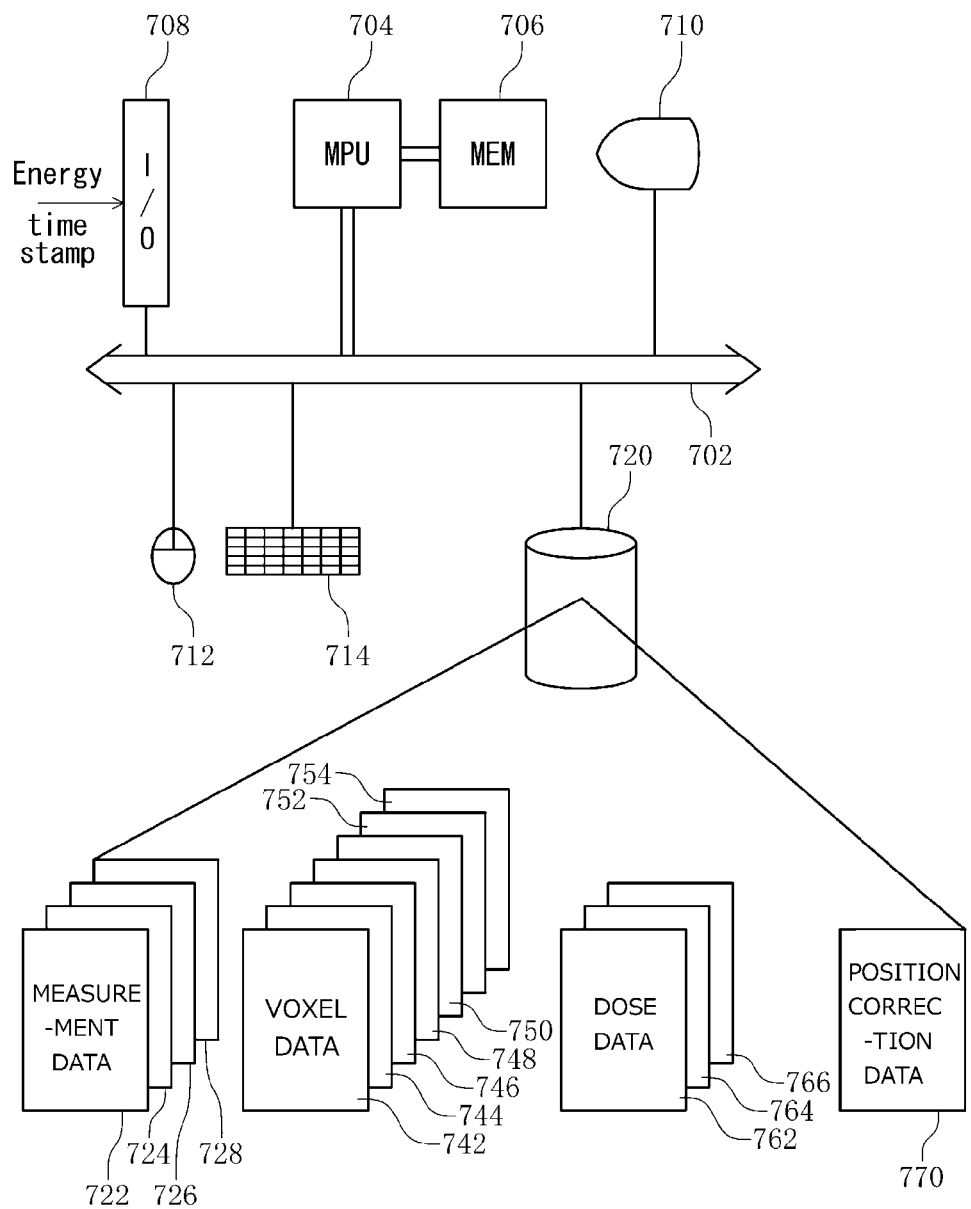
FIG. 7 is a block diagram showing a typical structure of a computer used in an embodiment of the present invention.
Figure 8:
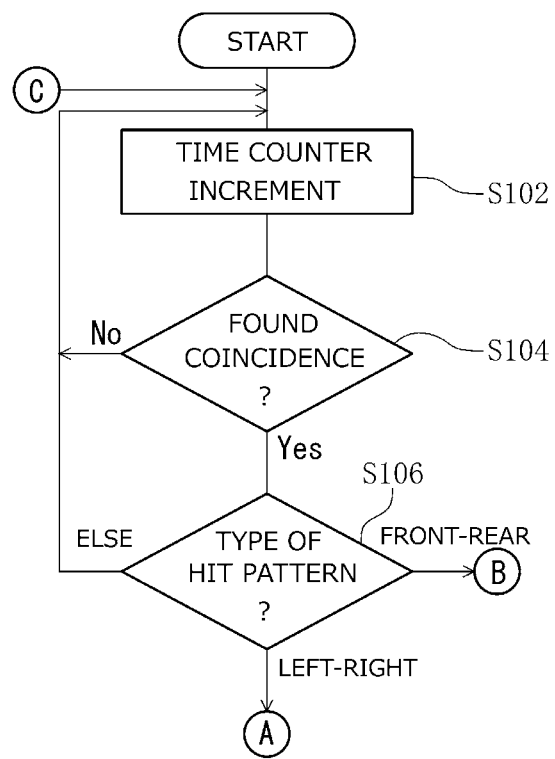
FIG. 8 is a flow chart showing processing using a computer for measurement data from gamma ray detection devices in an embodiment of the present invention, the processing being a determination processing as to whether PET imaging or Compton imaging should be applied for processing the detected events.
Figure 9:
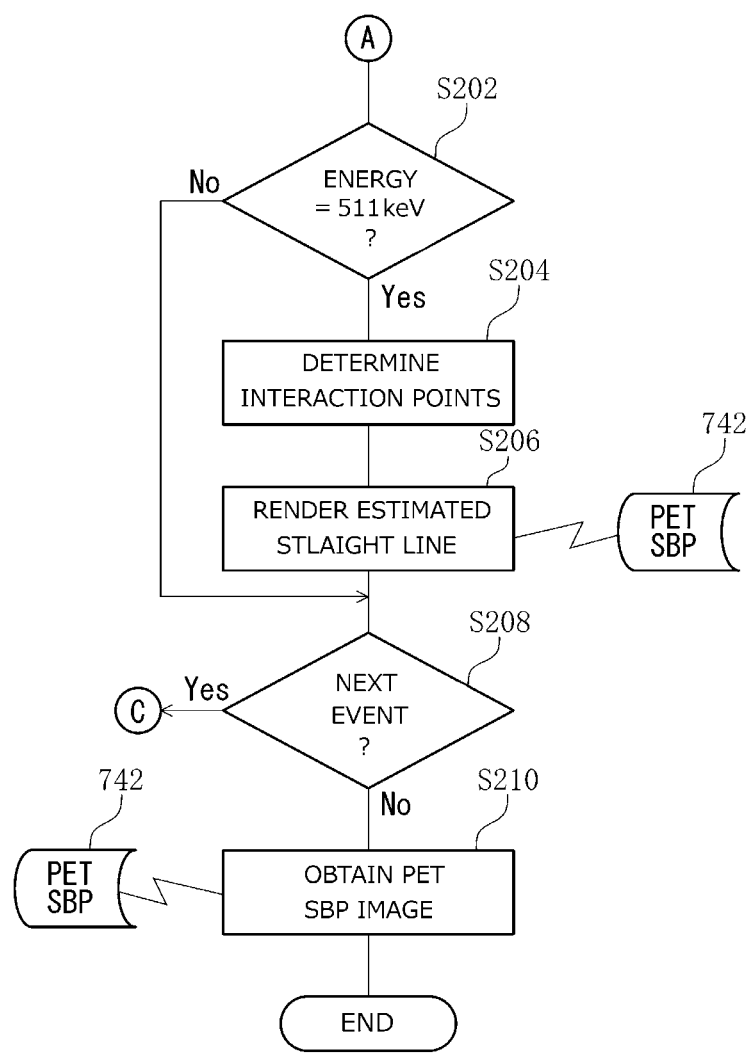
FIG. 9 is a flow chart showing an example processing on measurement data from gamma ray detectors using a computer in an embodiment of the present invention, the processing showing signal processing to obtain a PET SBP image.
Figure 10:
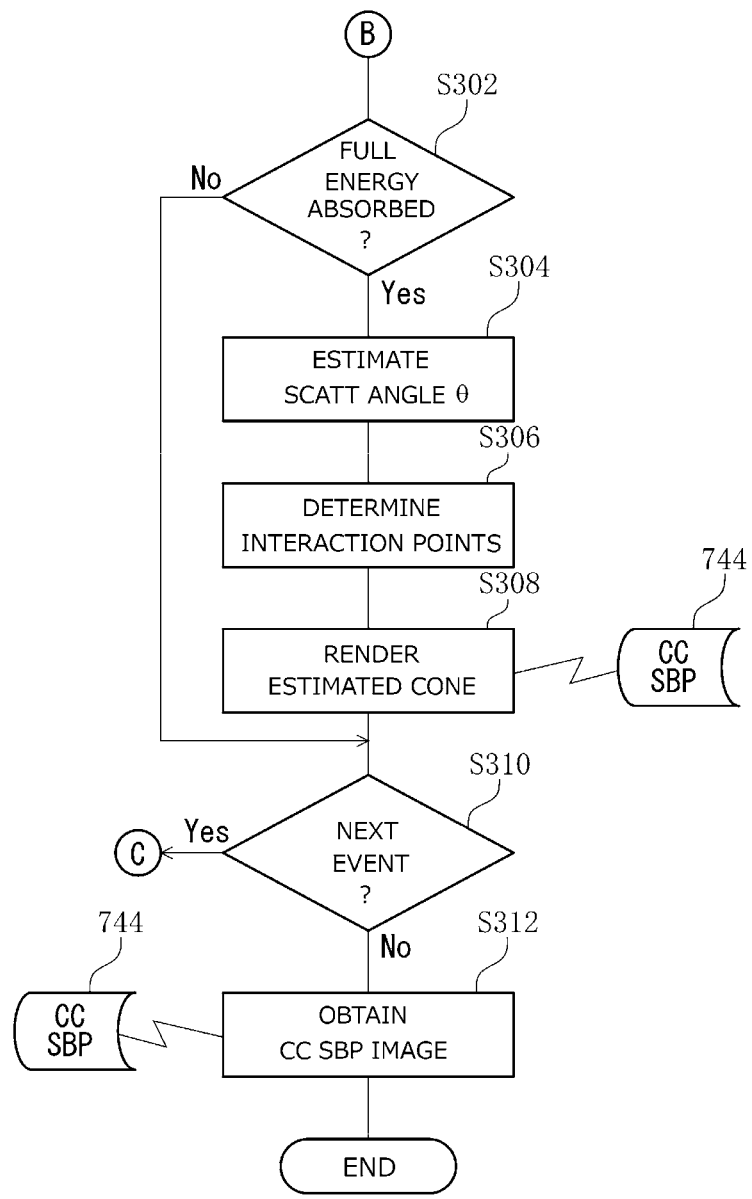
FIG. 10 is a flow chart showing an example processing on measurement data from gamma ray detectors using a computer in an embodiment of the present invention, the processing showing signal processing to obtain a CC SBP image.

FIG. 7 is a block diagram showing typical structure of the computer 690, and FIGS. 8-10 are flow charts showing steps for extracting process of events found to be coincident from measurement data from the gamma ray imaging device 100, and steps for differentiating process of PET imaging or Compton imaging based on the hit pattern. Note that FIG. 8 is a flow chart for determination processing to determine whether the detected gamma ray originated from the first or the second probe, and FIGS. 9 and 10 are flow charts showing series of processes to obtain PET image (or PET SBP image) and Compton image (CC SBP image) respectively.

As indicated in FIG. 7, a computer of common kind can be adopted for computer 690. That is, microprocessor unit (MPU) 704 is connected to appropriate bus 702, where the MPU 704 executes logical and arithmetic operations or controls program using memory (MEM) 706. Also connected to the bus 702 are input/output (I/O) 708 that receives energy information and time stamp from signal path 60 (FIG. 6) and display 710 for displaying necessary information by texts or images. On top of that, as in a general computer, provided to the computer 690 are mouse 712 and keyboard 714 for receiving operator's input.

Computer 690 is provided with storage 720 by a hard disk drive or the like. In the storage 720, logical structures are arranged for the first-fourth MDSs 722-728. The first-fourth MDSs 722-728 may be arranged as files that are organized by operating systems, for example. The first-fourth MDSs 722-728 store data from all strip electrodes from the semiconductor detectors respectively as in FIG. 6. Therefore, in the first MDS 722 for example, measurement data from twenty six strip electrodes of the first semiconductor detector 11 are stored in association with the time stamp data.

Simply put, when the computer 690 operates its reception function, MDUSPs from the first-fourth semiconductor detectors 11-22 are respectively stored into the first-fourth MDSs 722-728. The values in the energy field 612 in MDUSPs are associated with the time field 614 based on time stamp data from the clock generator 610. Thus it is possible to specify the measurement time or measurement time period when retrieving MDUSPs from the first-fourth MDSs 722-728. Operations of reception, data storing, and data retrieving as stated above are performed by MPU 704, which causes I/O 708 and the storage 720 to operate, based on instructions of a program stored in the computer 690, or based on instruction by an operator who instructs through the input means.

2-2-1. Determination of Coincidence Measurement

As indicated in FIG. 8, in the computer 690, a counter in MPU 704, hereinafter referred to as a "time counter" while not shown in figures, sets itself to a value that indicates time stamp data to be used in the retrieval. For example, the value of the time counter is incremented from the previous one (S102). Next, by correlating pieces of MDUSP with each other, where the pieces are retrieved based on time stamp data, determination for the coincidence measurement is made (S104). If this is explained in accordance with the context of data processing of the computer 690, parts of the MDUSP being associated to the time stamp data are retrieved, the parts are compared one another, and then determination is performed as to whether different semiconductor detectors detected events in coincidence or not.

Also note that such a comparison is made for one another among data obtained in an allowable time difference. The allowable time difference is a very short period of time, such as $10^{-9}$ through $10^{-7}$ seconds. The time stamp may be changed in a step of $10^{-8}$ seconds when the clock generator 610 (FIG. 6) generates clock pulses in the frequency of 100 MHz. For making coincidence measurement with the allowable time difference of $1.0\times10^{-8}$ seconds, values in the MDUSP having an exactly identical time stamp are selected, and each of them is compared with one another. The allowable time difference can be an arbitrary time difference as long as it is longer than the duration of pulses of the clock generator 610 (FIG. 6). For example allowable time difference of $1.0\times10^{-7}$ seconds is set as ten clocks when the clock operates in 100 MHz. In this case, ten values having consecutive time stamp data from the MDUSP can be selected for the coincidence measurement. The allowable time difference may be set to the same value as the increment step of the time counter, or as the pulse period duration of clock pulse, or may be set differently from the increment step of the time counter or the pulse period duration of the clock.

Since the allowable time difference is a time difference used for determining that the detections has occurred in coincidence, the value for the allowable time difference is set in consideration of various conditions. For example, the number of accidental coincidences, in which two gamma rays are generated accidentally or independently from pair annihilation but detected in two detectors in coincidence, should be reduced as much as possible. This is because such accidental coincidences would degrade measurement accuracy. Thus, the allowable time difference may be set as short as possible within the time resolution of detectors.

If coincidence is found among the measurement data (S104, branch Yes), then the process proceeds to determining hit pattern (S106), else the process returns back (S104, branch No) to increment of the time counter (S102) for processing next data. Note that the hit pattern determination may be performed only when the coincidence is found in at least two separate semiconductor detectors. Even if the MDUSP are found to record coincidence events, the hit pattern determination will not be performed so long as they are obtained from different strip electrode in a single semiconductor detector.

2-2-2. Determination of Hit Pattern

In determination of hit pattern (S106), a combination of semiconductor detector that detected gamma rays, or hit semiconductor detectors, is determined. If coincidence events obtained from the MDUSPs are indicating the fact that gamma rays are absorbed, for example, in both of the first and third semiconductor detectors 11 and 21 as illustrated with the coincidence finder 34 in FIG. 3, then it is highly likely that the events are attributable to gamma rays emitted by the first probe. In such a case PET imaging processing is performed. In contrast, if coincidence events obtained from MDUSPs are indicating the fact that detection signals are output from, for example, both of the first and second semiconductor detectors 11 and 12 as illustrated with the coincidence finder 32 in FIG. 3, and then it is highly likely that the events are attributable to gamma rays emitted by the second probe. In such a case Compton imaging processing is performed.

In determination of hit pattern (S106), a determination condition to proceed to the PET imaging is whether interactions with gamma rays are detected in coincidence in either of first or second semiconductor detectors 11 or 12 in the first Compton camera 10 and in either of the third or fourth semiconductor detector 21 or 22 in the second Compton camera 20, or not. It follows that four variations are possible in terms of the arrangement of FIG. 1. To make the description easily understood in connection with the first and second Compton cameras 10 and 20, which are depicted left and right in FIG. 1, the branch in FIG. 8 of the hit pattern leading to the PET imaging is labeled as "LEFT-RIGHT".

In contrast, in determining the hit pattern, a determination condition to proceed to the Compton imaging includes two cases: one is a case when detectors that detected the interactions with gamma rays in coincidence are the first and second semiconductor detectors 11 and 12 in the first Compton camera 10; and the other case is when such detectors are the third and fourth semiconductor detectors 21 and 22 in the second Compton camera 20. In connection with the fact that front and rear detectors have detected gamma rays in coincidence in such cases, the branch in FIG. 8 of the hit pattern leading to the Compton imaging is labeled as "FRONT-REAR".

When the hit pattern is neither "LEFT-RIGHT" nor "FRONT-REAR" (S106, branch "ELSE"), the process returns back to the beginning.

In accordance with the result of the hit pattern determination as stated above, the operation unit, such as a logical unit (not shown in figures) of the MPU 704, generates a PET determination signal or Compton scattering determination signal for controlling the program operation.

As indicated in FIG. 8, what is examined in the hit pattern determination processing (S106) is a combination of semiconductor detectors that detected interactions with gamma rays. At this step, differentiation is made between processing operation for the PET imaging and one for the Compton imaging based only on such determined combination. Also note that the hit pattern may be sufficiently reliable in determining whether the first probe or the second probe was the source of detected gamma rays. Therefore, gamma rays from the first and second probes would be used for the PET imaging and the Compton imaging. In actual situations, however, since various types of interactions may be possible between the gamma rays and semiconductor detectors depending on circumstances of a measurement target or a probe, hit pattern alone may not be sufficiently reliable to determine the type of the probe. For example, accidental coincidence, in which semiconductors in both sides detect events in coincidence because of other reason than pair annihilation, is rare but may happen. The typical examples for such cases are when dose amount of the second probe (gamma ray emitting nuclei for Compton imaging) is set high, or when detections are made under conditions with relatively longer allowable time difference. In preparation for such situations in the present embodiment, an additional determination is preferable on top of the differentiation due to the determination processing as to whether the PET imaging or the Compton imaging on the basis of the hit pattern at this step. In the additional determination, a determination using energies of the gamma rays is performed, and its result is reflected to imaging. The additional determinations will be described later in 3-1 and 3-2, together with image processing.

After finishing hit pattern determination (S106) as stated above, the PET imaging and/or the Compton imaging will be performed through an image processing depending on the determination result. In particular, a processor in the computer 690 outputs either of the PET determination signal or the Compton imaging signal in response to the determination result of the hit pattern, and the program operation is controlled accordingly. The steps following node A in FIG. 9 are carried out when the PET determination signal is output from the processor, whereas the steps following node B in FIG. 10 are carried out when the Compton scattering determination signal is output.

3. Image Processing: Generation of SBP Images

In the present embodiment, a computer is used for practicing the imaging processors 36 and 38 in FIG. 3. The processes for the imaging processing in the computer are almost identical between a case when implemented by using the signal processing by the circuit structure 40 and the coincidence measurement finder 50 in FIGS. 4 and 5, and another case when implemented by using the data processing in the measurement signal channels 60 in FIG. 6. Therefore, image processing is mainly described in the context of the data processing, and one in the signal processing is described later.

3-1. SBP Image for PET Imaging

FIG. 9 is a flow chart showing an image processing of an example process of a simple back propagation (SBP) in PET imaging. An image obtained by the process in FIG. 9 is a typical example of PET images. Such an image is referred to as a PET SBP image.

A case in which processing in FIG. 9 is performed is when the result of the determination processing of hit pattern S106 is "LEFT-RIGHT," which processing is indicated as a flow through node A, which connects FIGS. 8 and 9. That is, the process in FIG. 9 presumes a case when a gamma ray was detected in either of the first or second semiconductor detector 11 or 12 while another gamma ray was detected in either of the third or fourth semiconductor detectors 21 or 22. In such a case, the PET determination signal has been output by the processor. In the present embodiment, prior to the image processing, it is preferable that determination is performed as to whether energies of the gamma rays are considered to be 511 keV of the pair annihilation or not (S202). This is because, at the time of finishing the determination processing of hit pattern S106, the result may not directly mean that two detected gamma rays should be attributable to pair annihilation.

When the energy determination (S202) is included, rendering processes (S204 and S206) for PET imaging will be performed only when, for example, the energies of the gamma rays are considered to be 511 keV (S202, branch Yes). When the energies of the gamma rays are not considered to be 511 keV, the measurement data is not used specifically (S202, branch No). Note that, when energy determination is to be practiced it may be taken into account that various types of errors would be possible, such as insufficient accuracy in resolved energy values in each semiconductor detectors. Thus, energy values that are considered to be of pair annihilation are not limited to ones of exact energy value of 511 keV.

When the energy of the detected gamma rays are considered to be 511 keV, next, interaction points where gamma ray interacted with each semiconductor detector are determined (S204). In so doing, the interaction points are determined using the MDUSPs that have been obtained for each strip electrode, because each semiconductor detector is a multiple electrode planer germanium semiconductor detector. As indicated in FIG. 2, the multiple electrode planer germanium semiconductor detector has electrodes that are patterned to form a stripe pattern on front surface, or gamma ray entering surface, and rear surface, with directions of the stripe patterns on respective surfaces are crossing from each other. Among the measurement signal channels 60 (FIG. 6) of strip electrodes forming the stripe pattern, detection signal has been output from an electrode covering the point where the gamma ray was absorbed. Therefore, by searching through the MDUSPs from the first-fourth MDSs 722-728 for the energy value of the gamma ray, and by identifying the electrodes whose energy field contains such values of the gamma rays, it is possible to determine a point where the gamma ray interacted in the plate of each planer semiconductor detectors. Optionally, by relying on a time difference between signals from the front and rear strip electrodes for locating an interaction point, the interaction points in the thickness direction of the semiconductor plate, z direction in FIG. 2, may be accurately determined As a result, interaction points with gamma rays having energy of 511 keV are determined in either of the first or second semiconductor detector 11 or 12, both in the first Compton camera 10, and in either of the third or fourth semiconductor detector 21 or 22 both in the second Compton camera 20. Let position $P_1$ denote the determined interaction point in a step of determining interaction point S204, that is, an interaction point in either of the first or second semiconductor detector 11 or 12 in the first Compton camera 10 (first interaction point). Likewise, let position $P_2$ denote an interaction point in either of the third or fourth semiconductor detector 21 or 22 in the second Compton camera 20 (second interaction point). See FIGS. 1 and 3.

Next, rendering of estimated straight line (S206) is performed. The point where the gamma ray might well been emitted is a position that corresponds to or is adjacent to a point on straight line $P_1$-$P_2$, which connects points $P_1$ and $P_2$. Therefore the rendering operation is performed by changing memory values for each voxel corresponding to the straight line $P_1$-$P_2$ in a storage expressing three-dimensional space. In particular, stored values pointed by addresses that correspond indexes for identifying such voxels are changed in first voxel data storage (hereinafter referred to as "VDS") 742 in the computer 690.

Furthermore, determination is made as to whether a subsequent event exists or not (S208). In addition, when it was determined that the current event did not indicate the energy (511 keV) by pair annihilation (S202, branch No), such determination regarding the subsequent event is also made. Thereafter, when the existence of the subsequent event is recorded, the process returns to coincidence determination processing (S208, branch Yes, to node C in FIG. 8).

In contrast, if there is no subsequent event (S208, branch No), PET SBP image will be obtained, because all events have been already examined. At this step, voxel data for each position in the three-dimensional space are retrieved from the first VDS 742 (FIG. 7) that represent the three-dimensional space where the target is placed, and the voxel data are displayed on the display 710 of the computer 690 as needed. If memory values of the voxels in the storage indicate grayscale for example, the distribution image of radioactive source of gamma rays caused by pair annihilation (that is, the first probe) is obtained as a grayscale image that reflects overlap, or the multiplicity, of straight lines $P_1$-$P_2$.

It should be noted that the process in FIGS. 8 and 9 is just an example for obtaining an SBP image for PET imaging, and that the present embodiment includes other approaches that are similar to the above for obtaining a PET SBP image or its equivalents.

3-2. SBP Image for Compton Imaging

FIG. 10 is a flow chart showing an image processing of an example process including a simple back propagation (SBP) in Compton imaging. An image obtained by the process in FIG. 10 is a typical example of the Compton image. Such an image is referred to as a CC ("Compton camera") SBP image.

The cases in which processing in FIG. 10 is performed are a case when detectors generating determination signals of coincidence detection are the first and second semiconductor detectors 11 and 12 in the first Compton camera 10, and another case when such detectors are the third and fourth semiconductor detectors 21 and 22 in the second Compton camera 20. These cases are indicated as the result of "FRONT-REAR" in FIG. 8 of the determination processing. In such cases the Compton scattering determination signal has been output by the processor.

In the present embodiment, for calculating kinematics of Compton scattering, determination is made as to whether full-energy absorption occurred in the semiconductor detector or not (S302). Namely, determination is made as to whether energies $E_1$ and $E_2$, which were respectively detected in the front and rear detectors, satisfy a relationship $E_0=E_1+E_1$, where $E_0$ denotes initial gamma ray energy. Also keep in mind that $E_0$ is a known value and is determined according to a combination of a type of nuclei of gamma decay in the second probe and their decay scheme.

Thus, rendering processes (S304-S308) for Compton imaging is performed if the full-energy of the gamma ray is considered to be absorbed (S302, branch Yes). Otherwise, the measurement data is not used specifically (S302, branch No). This is because, even when Compton scattering occurred, the energy value has never been properly detected if the relationship $E_0=E_1+E_2$ is not satisfied, and such an incorrect energy value may well lead to an erroneous scattering angle for determining a conical surface.

If full-energy of the gamma ray has been absorbed, then the scattering angle θ is estimated based on kinematics of the Compton scattering (S304). The kinematics of the Compton scattering is calculated, for example, in accordance with the following mathematical relationship:

[Formula 1]
$$\cos\theta = 1 + m_0 c^2 \left( \frac{1}{E_0} - \frac{1}{E_2} \right) \quad (1)$$

where $m_0$ is rest mass of an electron, c is the speed of light in vacuum, $E_0$ is the initial energy of gamma ray, and $E_2$ is the energy detected in the rear detector. Note that the mathematical relationship of Formula (1) is adopted when the energy measurement accuracy or energy resolution of the rear detector is sufficient. If energy resolution of the front detector is high, another mathematical relationship between $E_0$ and $E_1$, which is easily derived from a relationship $E_0=E_1+E_2$ applied to the Formula (1), may be adopted.

Moreover, interaction points are determined (S306) in a similar fashion to PET imaging case (FIG. 9, S204). In this case also, by searching through the MDUSPs for energy field containing detected gamma ray energy, it is possible to determine a point where the gamma ray interacted in the plate of each planer semiconductor detector. In addition, by relying on a time difference between signals from the front and rear strip electrodes for specifying the interaction points, an interaction point in the thickness direction of the semiconductor plate, z direction in FIG. 2, may be accurately located.

Now let position $P_3$ denote an interaction point in front detector (third interaction point), or either of first or third semiconductor detector 11 or 21. Likewise, let position $P_4$ denote an interaction point in rear detector (fourth interaction point), or either of the second or fourth semiconductor detector 12 or 22. See FIGS. 1 and 3. The straight line $P_3$-$P_4$ indicates a line along which the gamma ray traveled after Compton scattering. Note that estimating scattering angle θ (S304) and determining the interaction points (S306) may be performed in parallel, or in reversed order.

Once the scattering angle θ and positions $P_3$ and $P_4$ are determined, direction of travel of the gamma ray before the Compton scattering is rendered (S308) based on an estimated surface of a cone. That is, the conical surface, or the estimated surface of the cone, is rendered using a storage for voxels in a storage that express the three-dimensional space where the target is placed, where the cone has $P_3$ as its apex, $P_3$-$P_4$ as its axis, and scattering angle θ as its half-angle at the apex. The rendering of the estimated surface of the cone is performed by changing memory values for each voxel corresponding to the estimated surface of the cone in a storage expressing three-dimensional space. Particularly in second VDS 744 in the computer 690 in FIG. 7, values being actually stored and pointed by addresses corresponding indexes for identifying such voxels are changed.

In cases when all processes S302-S308 as described above are completed for all events that are to be determined as Compton scattering events in the coincidence events and when the full-energy absorption has never been occurred (S302, branch No), the process returns to coincidence determination (S310, branch Yes, to node C in FIG. 8). In contrast, in a case when there is no subsequent event recorded (S310, branch No), then an SBP image that captured as Compton scattering event, or a CC SBP image, is obtained (S312). Also, as necessity, CC SBP images in the second VDS 744 are retrieved and their voxel data are displayed on the display 710 on computer 690. If memory values for the voxels of the CC SBP image are represented in grayscale for example then an image of the probe distribution that brought the gamma ray and detected by Compton scattering will be obtained with the grayscale representing overlap, or multiplicity, of estimated surfaces of cones.

It should be noted that the process through FIGS. 8 and 10 is merely an example for obtaining an SBP image for Compton imaging, and that the present embodiment includes other approaches that are similar to the above for obtaining CC SBP image or its equivalents.

3-3. SBP Image in Compton Imaging

On top of the forms of embodiment in which data processing using the measurement signal channels 60 and the computer 690 are adopted, PET SBP image and CC SBP image may be produced with image processing in another form of embodiment that adopts signal processing by using the circuit structure 40 and the coincidence measurement finder 50 indicated in FIGS. 4 and 5. In this form of the embodiment, PET imaging and Compton imaging are also performed in imaging processing in the computer 490 of the present embodiment. The imaging processing is performed similarly as described with reference to FIGS. 9 and 10.

Specifically, the computer 490 in FIG. 4 has first-fourth event data storages 492, 494, 496, and 498. Stored in the first-fourth event data storages 492-498 are data indicating signals that are determined as coincidence respectively from the first-fourth measurement signal channels. This means that in the circuit structure 40 indicated in FIG. 4, data transferred and stored in the computer 490 are not measurement data to which energy value and time stamp are associated (FIG. 6), but data for energy values after completing the same processing as the hit pattern determination processing (FIG. 5) by using OR gates 414A and 414B, and AND gates 416A, 416B, and 418.

In connection with the data for energy values, their hit patterns have been already determined, where each hit pattern specifies which of PET imaging or Compton imaging is to be performed. This is because such determination has been already made based on the PET determination signal (or output signal from AND gate 418 in FIGS. 4 and 5) and the Compton scattering determination signal (or output signals from AND gates 416A and 416B). Also note that, when PET determination signal and Compton scattering determination signal are recorded together with data of the energy values, the determination results of the hit pattern may be obtained. Moreover, even if such signal and data were not recorded, so long as information for associating data detected in coincidence with one another, such as event ID, is stored as data in the first-fourth event data storages 492-498, the determination result of the hit pattern may be easily reproduced. In either case, if data from the first-fourth event data storages 492-498 are used, the process indicated in FIG. 8 may be omitted. On top of that, the image processing for data from the first-fourth event data storages 492-498 is performed differently for each data according to whether the obtained data is associated with PET determination signal or Compton scattering determination signal. That is, of the data from the first-fourth event data storages 492-498, regarding data to be used in PET imaging, the process described in connection with FIG. 9 in Section 3-1 will be performed, whereas regarding data to be used in Compton imaging, the process described in connection with FIG. 10 in Section 3-2 will be performed. As stated above, producing PET SBP image and CC SBP image is also possible by using the data obtained from the circuit structure 40 in FIG. 4.

4. Improving Accuracy

In the present embodiment, accuracy of imaging, especially of Compton imaging may be improved by further data processing on voxel data for PET SBP image and CC SBP image. Note that the term "accuracy" may denote general quality of performances as is usually pursued in imaging that uses radioactive material. That is, accuracy may denote an S/N ratio in acquired images, resolution of details, and correlation between radioactivity values of readings from images and of actual values, and so on. The data processing that is used for improving accuracy in the present embodiment may include two typical approaches: one that uses data for voxels of a CC SBP image for improving accuracy in following processing, and the other that uses data of a PET SBP image for improving accuracy of voxel data for the of CC SBP image. Descriptions will be made first on noise filtering (4-1) and de-convolution (4-2), as processing for obtaining high accuracy images using a CC SBP image. Improving accuracy of CC SBP image will be described later, in "Improving Quantitative Performance through Comparison with PET image" (4-3). In the following descriptions a PET SBP image and a CC SBP image may refer to their respective voxel data.

4-1. Noise Filtering

Generally, noise originating from statistical fluctuation accompanies SBP images captured by Compton scattering events or CC SBP images. Therefore, it is useful to improve an S/N ratio by removing noise by noise filtering, which will be described as follows.

4-1-1. Determining Cutoff Frequency

Noise filtering of CC SBP images begins with Fourier transform on CC SBP images. That is, statistical fluctuation tends to be dominant in higher spatial frequency components in the CC SBP image. Therefore it would be effective for reducing noise to perform a Fourier transform on CC SBP image, and then to remove, or to reduce, high frequency components from its spectrum over the spatial frequency. A cutoff frequency in this procedure can be determined in various ways.

Examples for the cutoff frequency determination may include an "approach based on Fourier power spectrum," "operator's judgment with her visual checking upon filtering, " "statistical determination approach based on advance measurement such as PSF," and "determination by comparison with captured image for the identical target." The approach based on Fourier power spectrum is to convert a CC SBP image by a Fourier transform with spatial frequency and to determine a cutoff frequency thereafter based on the shape of its spectrum. The operator's judgment with her visual checking upon filtering is an approach in which cutoff frequency is determined by the visual judgment based on the operator's experiences. The statistical determination approach based on advanced measurements such as PSF is to make preliminary measurement for investigating noise comportment inspection produced in the measurement system in advance and to determine cutoff frequency based on a frequency spectrum of statistically fluctuating noise. The "determination by comparison with captured image for the identical target" will be described later (in Section 4-3-2-5) together with another approach that uses a PET image.

4-1-2. Filter Application

After determining the cutoff frequency, a filter will be defined based on the cutoff frequency. In a typical situation, higher frequency comportments than the cutoff frequency are totally removed. In addition, a filter expressed by a function that gradually reduces frequency components in frequency higher than the cutoff frequency, such as a Butterworth filter as in Formula (2), may be adopted.

[Formula 2]

$$\text{Intensity}(w) = \frac{1}{\left(1 + \left(\frac{w}{w_c}\right)^{2n}\right)} \quad (2)$$

where w denotes a spatial frequency, $w_c$ is the cutoff frequency and n is an arbitrary integer number. The final image will be obtained by performing an inverse Fourier transform on frequency components to which the filter was applied.

4-2. De-Convolution

Next described is improving spatial resolution for details by performing de-convolution to remove effects of position-response function. A CC SBP image that is not processed with noise filtering will be processed. The modeled relationship between a CC SBP image and a true image based on a position-response function, which takes the form of a pointed spread function or a PSF, is expressed as:

[Formula 3]

$$^C n_i = \sum_j {}^C p_{ij} {}^C \lambda_j. \quad (3)$$

Note that, $^C n_i$ is a voxel value of index i for a position, or a voxel value of position i, in the CC SBP image, $^C p_{ij}$ is a position-response function indicating contributions of spread from a position indicated by index j ("position j") to position i, and $^C \lambda_j$ is a voxel values at position j for the true image. Note that left superscript character C for each variable is an indication meaning that the variable is used for Compton imaging. As such, the right-hand side of Formula (3) shows that the CC SBP image $^C n_i$ is expressed by a convolution of the true image $^C \lambda_j$ and the position-response function $^C p_{ij}$ over position j.

In Formula (3), the position-response function $^C p_{ij}$ represents a contribution of a voxel value at position j to position i. Therefore, if we express the convolution by asterisk (*), Formula (3) is rewritten as:

(CC SBP image)=(position-response function*true image), where the position-response function is a point spread function in Formula (3). The point spread function represents values of each position or each voxel of a CC SBP image, under an assumption that the CC SBP image has been obtained with gamma rays that were emitted from a mathematical point. A process to obtain a true image by removing effects of position-response function from the captured CC SBP image can be performed in two ways: de-convolution using constant PSF and de-convolution using position dependent PSF.

4-2-1. De-Convolution Using Constant PSF

First, the description is made with an assumption that position-response function does not dependent on position throughout processing the modeling as described above, or an assumption of constant PSF. With this assumption, a CC SBP image, which is represented by convolution of a true image and the position-response function, has a general characteristic that it is expressed by multiplication after Fourier transform. From this nature, de-convolution can be processed by applying Fourier transform. When the position-response function p does not depend upon position, performing Fourier transform to both sides of Formula (3) yields

[Formula 4]
$$^C\Lambda_s = \frac{^CN_s}{^CP_{ss}}. \qquad (4)$$

In this expression, s is an index for specifying spatial frequency vector in three-dimensional space, $^C\Lambda_s$ is a Fourier transform of true image $^C\lambda_j$, $^CN_s$ is a Fourier transform of CC SBP image $^Cn_i$, and $^CP_{ss}$ is a Fourier transform of position response function $^Cp$. The reason why formula (4) gives Fourier transform $^C\Lambda_s$ of a true image $^C\lambda_j$ is that Fourier transform $^CP_{ss}$ of position-response function $^Cp$ is diagonalized with index s when position-response function $^Cp_{ij}$ is independent of position. The right-hand side of Formula (4) is easily calculated because it has a division form of (Fourier transform of measurement image)/(Fourier transform of position-response function).

Also note that the filter described in Section 4-1 can be applied to Formula (4) to remove statistical noise. In such a case, if we let $W_s$ be a filter function that is defined in frequency space, filter processing

[Formula 5]
$$^C\Lambda_s = \frac{W_s\, ^CN_s}{^CP_{ss}} \qquad (5)$$

is used for computing Fourier transform $^C\Lambda_s$ of a true image $^C\lambda_j$. A useful filter function $W_s$ that may be adopted is not necessarily a Butterworth filter as described in Formula (2). For example, a Wiener type filter may also be useful. To have the true image $^C\lambda_j$ from Formula (5), inverse Fourier transform on $^C\Lambda_s$ is carried out.

4-4-2. De-Convolution Using Position Dependent PSF

Actual Compton images often have different position-response functions, such as in the center area and the periphery within each image. Therefore, rather than using a constant PSF, adopting a position-response function that depends on voxel position or position dependent PSF in the modeling is preferable for obtaining more accurate image in Compton imaging. Described below is processing of de-convolution for a case in which position dependent PSF is used.

When a position dependent PSF is adopted, it is possible to perform de-convolution by successive accuracy improvement of a true image by iteration. That is, assume a sequence of voxel value $^C\lambda_j^{(m)}$ that converges to each voxel value $^C\lambda_j$ of the true image, where m is an integer number greater than or equal to 0. First, an initial value $^C\lambda_j^{(0)}$ of the iteration is numerically computed according to the following form:

[Formula 6]
$$^C\lambda_i^{(0)} = \frac{1}{N}\sum_{i=1}^{N} {^Cn_i}, \qquad (6)$$

where N is an integer indicating the number of voxels included in a volume through which the position dependent PSF is assumed. Then successive numerical computations are carried out based on a recurrence equation for obtaining $^C\lambda_j^{(m+1)}$ from $^C\lambda_j^{(m)}$, or

[Formula 7]
$$^C\lambda_j^{(m+1)} = {^C\lambda_j^{(m)}} + \sum_i \left({^Cn_i} - \sum_k {^C\lambda_k^{(m)}}\, ^CP_{ik}\right)\, ^Cp_{ij}. \qquad (7)$$

In the course of iteration through this recurrence equation with incrementing m, the $^C\lambda_j^{(m)}$ converges to $^C\lambda_j$ of the true image. This is because Formula (7) has a form:

((m+1)th image)=(mth image)+((CC SBP image)−
(convolution image by PSF of mth image))×PSF, where (mth image) denotes $^C\lambda_j^{(m)}$ and so on, and in this expression the indication of summation over i is omitted. More specifically, in the second term of the right-hand side in Formula (7), a factor in the parenthesis that is to be multiplied by the position dependent PSF represents residual that has not yet been included in (mth image) based on Formula (3). Therefore, summation over i after multiplying position dependent PSF to the residual portion, or the second term in the right-hand side of Formula (7), is a term for reflecting the residual portion that have not yet been included in the mth image via the position dependent PSF. As a result, when the residual portion is added to the first term of the right-hand side of Formula (7), or mth image, then the next (m+1)th image will be obtained. This means that, performing iteration for numerical computations of $^C\lambda_j^{(m)}$ according to Formulas (6) and (7) produces an approximate numeric value sufficiently close to $^C\lambda_j$. To carry out the numerical computations according to Formulas (6) and (7), a CC SBP image $^Cn_i$ is retrieved from the second VDS 744 and is substituted into Formulas (6) and (7).

Figure 11:
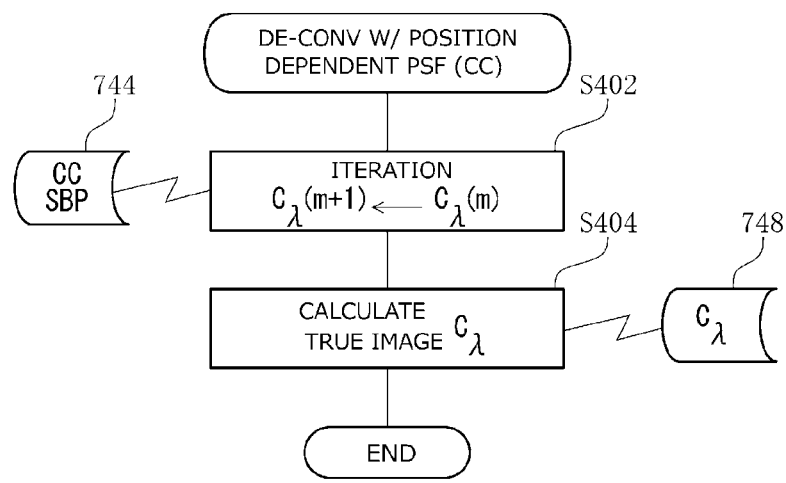
FIG. 11 is a flow chart showing processing of de-convolution with a position dependent PSF in an embodiment of the present invention.
Figure 11:
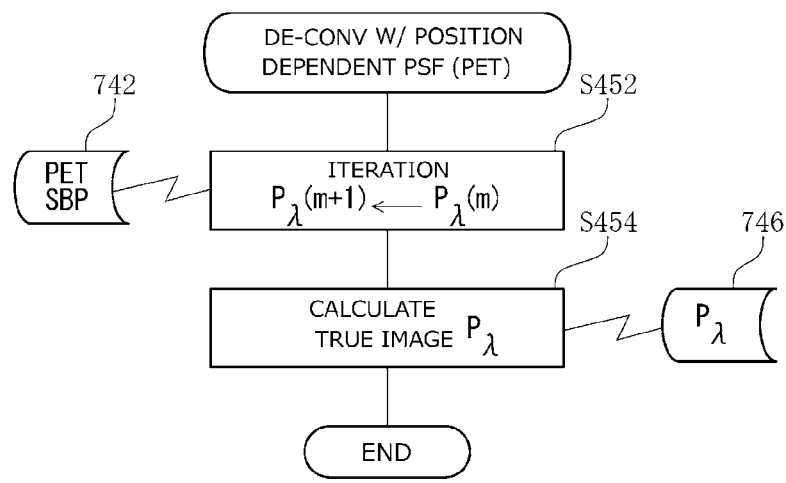

FIG. 11 is a flow chart showing processing of iterations of the numerical computation for the true value $\lambda_j^{(m)}$. FIG. 11(a) shows an iteration processing for Compton imaging. Regarding FIG. 11(b), description will be made later. To perform the iteration as described above by computer 690, first, voxel value $^Cn_i$ of position i is retrieved from CC SBP image stored in the second VDS 744 (FIG. 7), and iteration calculation is carried out according to Formulas (6) and (7) (S402). Although the number of repetition for the iteration is not specified, the iteration is performed until each voxel value is found to be convergent from a practical point of view. Then the true image of Compton image is obtained and stored to the fourth VDS 748. Note that computation to perform the iteration needs only four fundamental rules of arithmetic for each voxel value and thus can be carried out easily by successive calculation using such as the fourth VDS 748, to which true image of Compton image is stored, and the other storage if necessary.

The process mentioned above makes it possible to compute true image $^C\lambda_j$, even when its position dependent PSF has a complicated dependency to positions. In such a case, it would be useful if we make a model for a position dependent PSF $^C p_{ij}$ in such a manner that it changes its shape over the voxel positions according to some kind of parameters, for example. If the model is applied to the computation of Formula (7), it is possible to obtain values of true image $^C\lambda_j$ as necessity. Furthermore it is also useful to apply filter functions that were described in Section 4-1 by using Fourier transform and inverse Fourier transform framework.

4-3. Improving Quantitative Performance Through Comparison with PET Image

In the present embodiment, it is possible to improve image resolution and quantitative performance of Compton imaging in combination with voxel data of PET imaging. For that purpose, the PET images are obtained with the same probe for the Compton image, and a calibration procedure will be performed for correcting characteristics on detection or processing for the Compton imaging.

Figure 12:
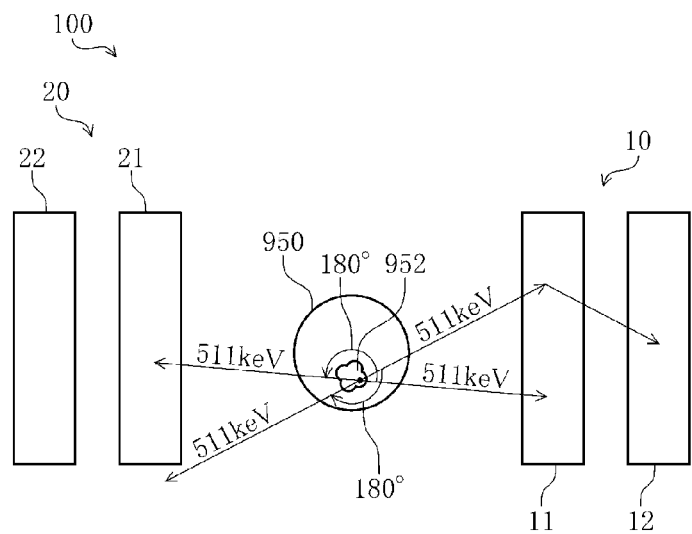
FIG. 12 is a schematic cross sectional view showing cases when both of PET imaging and Compton imaging are processed using gamma rays emitted by the first probe administered to the imaging target in an embodiment of the present invention.

FIG. 12 is a schematic cross sectional view showing cases when both of PET imaging and Compton imaging can be processed using gamma rays emitted by the first probe administered to the imaging target 950 in the gamma ray imaging device 100 in the present embodiment. The configuration regarding the gamma ray imaging device 100 with the imaging target 950 is the same as the gamma ray imaging device 100 with the imaging target 900 in FIG. 1. The first probe administered to imaging target 950 in FIG. 12 distributes over living body region 952. Also note that FIG. 12 does not indicate a second probe because whether the second probe is administered to the imaging target 950 or not is optional.

What are emitted from the imaging target 950 and used for imaging are gamma rays of pair annihilation having energy of 511 keV originating from the first probe. A pair of gamma rays is emitted into opposite directions of substantially 180 degrees from each other at the position of pair annihilation, which is each part of the living body region 952 where the first program distributes. The images captured by PET imaging are those obtained when each gamma ray of the pair is detected by the first and second Compton cameras 10 and 20. In contrast, the images captured by Compton imaging are those obtained from a gamma ray of 511 keV that is scattered by Compton scattering in front detector and the full-energy absorption takes place in the rear detector for the gamma ray after the scattering, in the first or second Compton camera 10 or 20. It follows that, by adopting an identical probe of identical distribution for acquiring PET and Compton images, calibration can be processed to compensate Compton cameras' characteristics by using a PET image.

4-3-1. Capturing PET Images

The calibration process is performed as follows. First, Compton and PET images are captured from the imaging target 950 having the identical probe of identical distribution. The capturing of Compton image is processed typically in such a manner as mentioned earlier in Sections 4-1 and 4-2, thereafter the noise is reduced, and the Compton image is obtained as a de-convoluted image. The capturing of the PET image is also processed from a PET SBP image to obtain a noise reduced and de-convoluted PET image in such a manner as mentioned earlier in Sections 4-1 and 4-2 for obtaining a Compton image from a CC SBP image. In this context recursive equations for iteration that are similar to Formulas (6) and (7) may also be used for the PET SBP image, as necessity for obtaining the PET image. Therefore the following recursive equations are used to obtain the de-convoluted PET image,

[Formula 8]

$$\begin{cases} ^P\lambda_j^{(0)} = \frac{1}{N}\sum_{i=1}^{N} {}^P n_i \\ ^P\lambda_j^{(m+1)} = {}^P\lambda_j^{(m)} + \sum_i \left({}^P n_i - \sum_k {}^P\lambda_k^{(m)\,P} p_{ik}\right){}^P p_{ij} \end{cases} \quad (8)$$

where m is an integer number greater than or equal to 0, $^P n_i$ is a voxel value of index i indicating a position in a PET image, $^P p_{ij}$ is a position-response function for PET images, the position-response function depending on its position and indicating contributions of spread from a position indicated by index j ("position j") to position i, and $^P\lambda_j^{(m)}$ is a sequence representing voxel values $^P\lambda_j$ at position j for a true image of the PET image. Note that left superscript character P for each variable is an indication meaning that the variable is used for the PET imaging. The PET SBP image $^P n_i$ for calculating the right-hand side of first line of Formula (8) is retrieved from the first VDS 742 (FIG. 7).

FIG. 11(b) indicates iteration processing based on Formula (8). First, in the iteration for PET image also, voxel value $^P n_i$ of position i of the PET SBP image is retrieved from the first VDS 742 (FIG. 7) as similarly in FIG. 11(a), and the iteration is performed (S452). After converged voxel values are obtained through the iteration, a true image of the PET image is obtained (S454) and then stored into third VDS 746.

4-3-2. Calibration Through Blank and Transmission Measurements (for PET Imaging)

In PET imaging, since the image capturing mechanism of coincidence measurement of gamma rays created by pair annihilation is adopted, it is possible to carry out the measurement with high quantitative performance reflecting absorbance (attenuation coefficients) for gamma rays in the imaging target. For that purpose blank and transmission measurements are made in the PET imaging. Note that to avoid possible errors in actual situations, such as degraded reproducibility of position alignment caused by repositioning of the imaging target in practicing the measurement, measurements are made first for a blank measurement, then for the PET imaging, and lastly for a transmission measurement concerning the target image. The data obtained from blank and transmission measurements are utilized for improving quantitative performance in data processing for the PET imaging.

Blank measurements are those measurements that are made without disposing the imaging target and are practiced repeatedly while changing the position of a radioactive source for PET imaging, whose positions are where the coincidence measurement is possible but outside of an imaging target, such as in a ring sufficiently larger than the imaging target. The measurement data obtained through such measurements is called blank PET measurement data and stored into first dose data storage 762 (FIG. 7). The blank PET measurement data is data that indicates radioactivity for each direction of travel of the gamma ray. Hereinafter, a "line" may denote a line on which gamma ray travels after the emission.

In contrast, the transmission measurement is a measurement while the imaging target is properly placed. The measurement utilizes a nature in which the absorbance of gamma rays do not depend on pair annihilation positions so long as the position is on a single straight line that crosses gamma ray absorbing material. Also note that this nature is true for inside or outside of such imaging target as living body in which the pair annihilation occurred with absorption. Therefore similarly to blank measurement, repeated measurements outside of the imaging target while changing positions where coincidence measurement is possible may enable us to obtain measurement data for radioactivity for each line along which gamma ray travels from the imaging target when absorption occurs in the imaging target. Then the measurement data is stored to second dose data storage 764 (FIG. 7) as transmission PET measurement data, where the measurement data are obtained by the transmission measurement and related to each line that passes through the imaging target.

It should be noted that comparing the PET measurement data in the first dose data storage 762 and the transmission measurement data in the second dose data storage 764 makes it possible to provide each line's gamma ray absorbance while removing detector efficiency. That is, positional dependency of detection efficiency for each part of semiconductor detector, or detector response, is identical for both measurements of transmission measurement data and blank PET measurement data. Therefore, if difference between them is computed, then effects of the detector response are cancelled to yield only contributions of gamma ray absorption for each line of the imaging target. Also based on such measurements, the gamma ray absorbance of each position in the imaging target is derived in the three-dimension.

Figure 13:
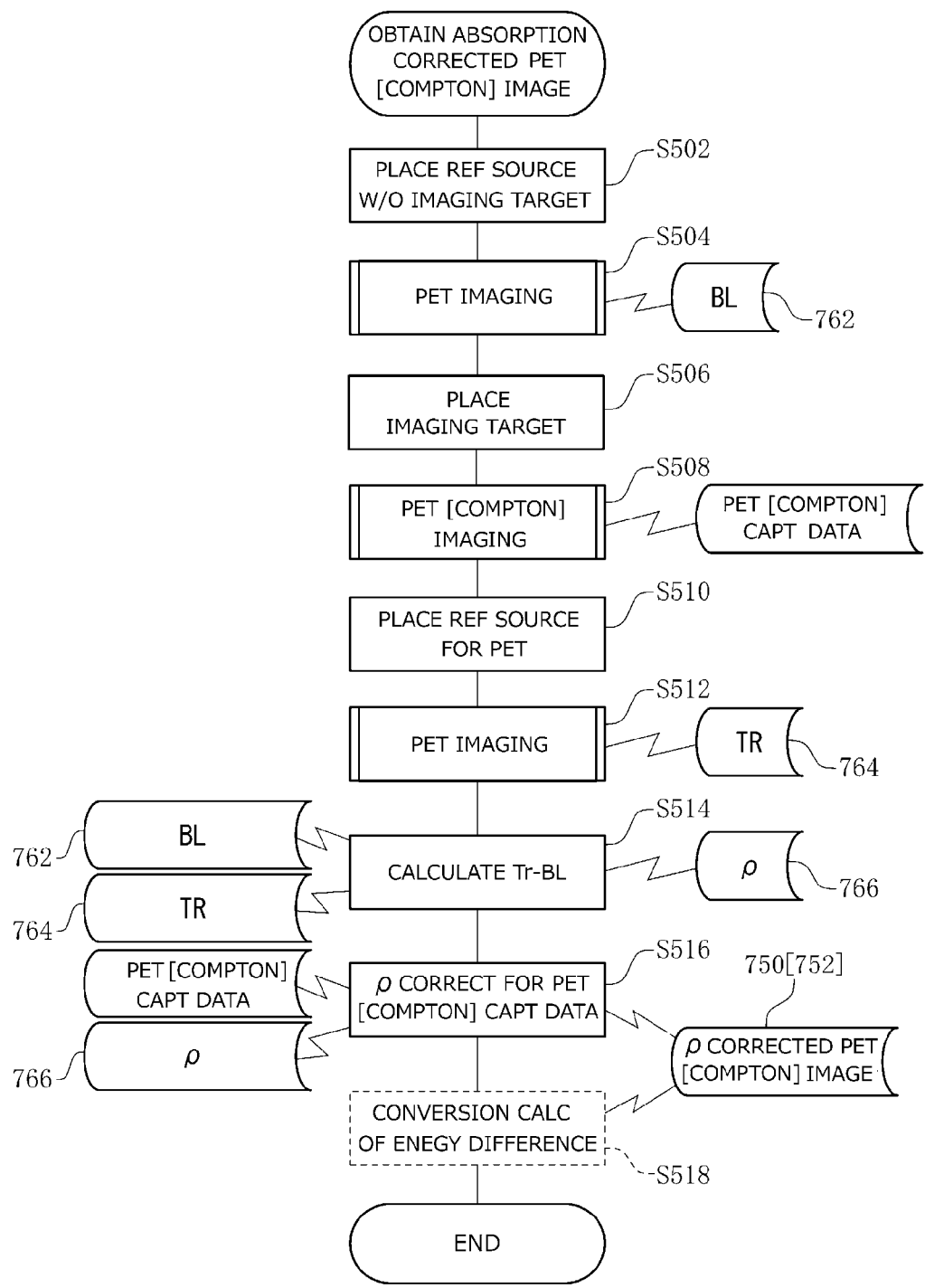
FIG. 13 is a flow chart showing measurement steps and data processing steps that are used for correcting absorbance in the imaging target for PET images and Compton images in an embodiment of the present invention.

The specific steps of the blank and transmission measurements are made as indicated in FIG. 13. FIG. 13 is a flow chart showing measurement steps and data processing steps for correcting absorbance of the measurement target on PET and Compton images in the present embodiment. The outline of the processing is that the capturing or measurement is performed in the first half (S502-S512), and that the data processing for correcting absorbance is in the second half (S514-S516). In the measurements, first made is blank measurement (S502-S504), followed by PET imaging (S506 and S508), and lastly transmission imaging (S510 and S512).

In the blank measurement, a reference radioactive source for PET imaging is used without disposing an imaging target (S502) to perform PET imaging as blank measurement (S504). For example, a germanium 68/gallium 68 ($^{68}$Ge/$^{68}$Ga) source may be selected as the reference radioactive source. The blank measurement is practiced as described above, by placing the radioactive source for PET imaging in a ring sufficiently larger than an imaging target and repeating the measurement while changing its position. The obtained data is called blank PET measurement data and is stored into the first dose data storage 762.

Next, the PET imaging with placing an imaging target is performed. In this PET imaging, an imaging target to which a first probe is administered is placed (S506). The configuration of the imaging target is the same as in FIG. 12. Then the PET imaging is performed for the imaging target (S508). Note that what are performed in the PET imaging S508 out of processes already described with reference to FIGS. 4-10 are those until the data of PET imaging is obtained. That is, what are performed in this PET imaging S508 are either storing data indicating coincidence measurement from the first-fourth measurement signal channels to the first-fourth event data storages 492-498, or storing the MDUSP to the first-fourth MDSs 722-728. Hereinafter the data is called as PET capturing data for explanation purposes.

Thereafter, a reference source for PET imaging is placed between the first and third semiconductor detectors 11 and 21 and outside of the imaging target (S510), and then PET imaging as transmission measurement is performed (S512). The PET imaging is performed by repeated measurements with placing the radioactive source for PET imaging while changing its position in a ring sufficiently larger than an imaging target, as described above. The data obtained are stored into the second dose data storage 764 as the measurement data of transmission PET measurement data.

Then, the data processing using such data is performed. First, computing the detector response and correcting absorbance for the PET capturing data are carried out (S514 and S516). The detector response is computed using blank PET measurement data from the first dose data storage 762 and transmission PET measurement data from the second dose data storage 764. That is, these pieces of data are used for calculating difference data, which is obtained by subtracting transmission PET measurement data from blank PET measurement data in each line, and the difference data is stored into third dose data storage 766 (S514). The difference data in the third dose data storage 766 is data of contributions of gamma ray absorbance only for each line in the imaging target whose positional dependence of the detector efficiency has been cancelled. Then, the difference data for each line of the imaging target in the third dose data storage 766 is used for correcting absorbance (S516) for the PET captured data obtained in PET imaging S508.

The processing of the correcting absorbance of PET captured data (S516) is one slightly modified from FIG. 9. The modification is made on the rendering process of the estimated lines (S206). More specifically, in the rendering processing of the estimated line, gamma ray absorbance in a line corresponding to each estimated line is used. The use of the absorbance is done by dividing values of changes for changing voxel data for each point corresponding to each estimated line by transmittance of gamma rays of the same line of, or of a line adjacent to, the estimated line reaching from the point to the detectors. Note that such processing is easily performed because the transmittance on each line satisfies a simple relationship with the absorbance of each line, as (transmittance) =1−(absorbance). As a result, PET SBP image with correction of absorbance, or absorbance-corrected PET image, is obtained and stored into fifth VDS 750. Also note that the absorbance-corrected PET image is substantially accuracy improved one of the PET SBP image stored in the first VDS 742. The data is hereinafter called absorbance-corrected PET image, and a storage that stores this data is denoted as the fifth VDS 750, for clear description purposes only. This means that, the absorbance-corrected PET image from the fifth VDS 750 may be selected as a target of the data processing as in the de-convolution as described in Section 4-3-1, in place of the PET SBP image from the first VDS 742.

4-3-3. Calibration of Compton Images Based on PET Images

The Compton imaging in the present embodiment may take advantage of the high accuracy nature of PET imaging. In particular, a combination of the PET imaging and the Compton imaging both performed over an identical probe as indicated in FIG. 12 enables improvement of capturing accuracy in Compton imaging. In this Section, five approaches are described in detail that may result in accuracy improvement of captured data of Compton imaging based on PET imaging. The first approach addresses absorbance of imaging target (4-3-3-1). The second approach handles a correction of positional changes in detection efficiencies, or calibration of detector responses (−2). The third approach improves accuracy of position-response function for de-convolution (−3). The fourth is for positional alignment (−4). Lastly, the fifth approach is regarding determination schemes of cutoff frequencies (−5).

4-3-3-1. Calibration Through Blank and Transmission Measurements (for Compton Imaging)

As described in Section 4-3-2, it is possible in the PET imaging to perform quantitative measurement on absorbance of gamma rays, or attenuation coefficients, along each line in the imaging target through the transmission measurement. The data obtained in such a manner is data of gamma ray absorbance that may have effects on measurement values on each line in the imaging target stored in the third dose data storage 766 in the computer 690. Although the gamma ray absorbance was measured through PET imaging, it is also applicable to Compton imaging. This is because gamma rays used in image capturing for both the PET imaging and Compton imaging are only those that are obtained outside of imaging target through which the gamma rays traveled and attenuated by the absorption. Therefore, in the process for correcting absorbance S516 for PET capturing data in FIG. 13, a process to reflect gamma ray absorbance on each line may be performed also for the Compton imaging. The process to reflect the absorbance is performed in the process of rendering the estimated conical surface in the Compton imaging (FIG. 10, S308) based on the gamma ray absorbance in each position of the imaging target stored in the third dose data storage 766. In particular, such process is performed by dividing a value for changing voxel data for each position on the generatrix of the estimated conical surface by the transmittance of the gamma ray in the imaging target along a line from the position to the detector.

Note that gamma ray absorbance measured by PET imaging is obtained from gamma rays of 511 keV originated by pair annihilation. Therefore, it is reasonable that the absorbance for each line in the imaging target obtained by the transmission measurement of the PET imaging is applied to Compton imaging of 511 keV gamma ray. Moreover from a practical point of view, it is also possible that absorbance for gamma ray other than 511 keV is calculated using absorbance for 511 keV. This is because energy dependence of the absorbance for respective material are well-studied in general, and it is easy to convert the absorbance of the imaging target for 511 keV measured in PET imaging to one for gamma rays used in Compton imaging.

The process for such correction is substantially the same as described for absorbance correction in PET imaging in Section 4-3-2 with reference to FIG. 13. In this regard, FIG. 13 also indicates a process flow applicable to the absorbance correction in the Compton imaging in parenthesis with square brackets ("[" and "]"). That is, similarly to PET imaging, the measurement is made in the first half (S502-S512) and the data processing is in the second half (S514-S516). Similarly to the PET imaging, the blank measurement (S502 and S504) is processed at the beginning in the measurement, and transmission imaging (S510 and S512) is performed in the end. The differences in the processing from one for the absorbance correction in the PET imaging are that Compton imaging (S506 and S508) is performed in place of the PET imaging, and that another detailed processing in the absorbance correction (S516) is performed for the Compton capturing data. The absorbance correction in the Compton imaging will be described further by focusing on the differences from the absorbance correction in the PET imaging.

In the beginning of the process to reflect the absorbance of gamma ray into the Compton imaging, blank measurement is made (S502 and S504). Upon completion of the blank measurement, Compton imaging with placing the imaging target is performed. In this Compton imaging, an imaging target is placed, while at least one of the first or second probe is administered to the imaging target (S506). In so doing it does not matter whether the other of the first and second probes is administered to the imaging target or not. Then the Compton imaging is performed concerning the imaging target placed as in FIG. 12 (S508). Similarly as in the PET imaging case, what are performed are those for obtaining the data of Compton imaging, that is, those either for storing data indicating coincidence measurement from the first-fourth measurement signal channels to the first-fourth event data storages 492-498 as described with reference to FIGS. 4-10, or for storing the MDUSP to the first-fourth MDSs 722-728 through signal paths in FIG. 6. The data obtained through the process is called Compton capturing data. Thereafter transmission measurement is made (S510 and S512).

In the data processing detector response is calculated (S514) as in the absorbance correction regarding PET capturing data, then absorbance correction for the Compton capturing data (S516) is performed. In the absorbance correction of Compton capturing data (S516), difference data stored in the third dose data storage 766 is used. The difference data in the third dose data storage 766 is identical to one for absorbance correction of PET images. The difference data for each line in the imaging target in the third dose data storage 766 is used for absorbance correction of Compton capturing data obtained in the Compton imaging (S508).

The process in the absorbance correction (S516) is a slightly modified process from one indicated in FIG. 10. The modification is made on rendering process of estimated conical surfaces (S308). In particular, in the rendering process of the estimated conical surface, the absorbance of gamma rays in the imaging target in each direction of generatrix for the estimated cone faces is used. The use of the absorbance is done by dividing values of changes for changing voxel data for each point on each generatrix of the estimated conical surface by transmittance of gamma rays of a line reaching from the point to the detectors. Therefore, the absorbance correction for Compton capturing data is substantially the same process as the absorbance correction for PET capturing data. As a result, a CC SBP image with correction of absorbance, or an absorbance-corrected Compton image is obtained and stored into sixth VDS 752.

Note that, as a difference point from the absorbance correction for PET image, absorbance (transmittance) correction for converting the difference caused by the energy difference in gamma rays (S518) can be adopted for accuracy improvement of the Compton image. This correction is made in a case when a probe used in the Compton imaging emits gamma rays other than 511 keV. The correction of the absorbance in such a case is carried out as conversion calculation processing to reflect a variation between an absorbance for 511 keV gamma ray and one for gamma ray of the Compton imaging. Also in this case the absorbance-corrected Compton image is stored in the sixth VDS 752.

That the absorbance-corrected Compton image is substantially the accuracy improved one of the CC SBP image stored in the second VDS 744 is the same for the absorbance correction for PET images. Therefore, the target to which the data processing is performed, such as de-convolution as described in Section 4-2, may be the absorbance-corrected Compton image from the sixth VDS 752, in place of CC SBP image $^C n_i$ from the second VDS 744.

4-3-3-2. Calibration of Detector Response Through Compton Imaging

As described in Section 4-3-3-1, the position dependence of the detector efficiency, or detector response, has been cancelled in the absorbance correction processing for the Compton imaging, after the blank measurement and the transmission measurement for the PET imaging. As such, the calibration of detector response in the Compton imaging can be carried out by blank measurement of the PET imaging.

Figure 14:
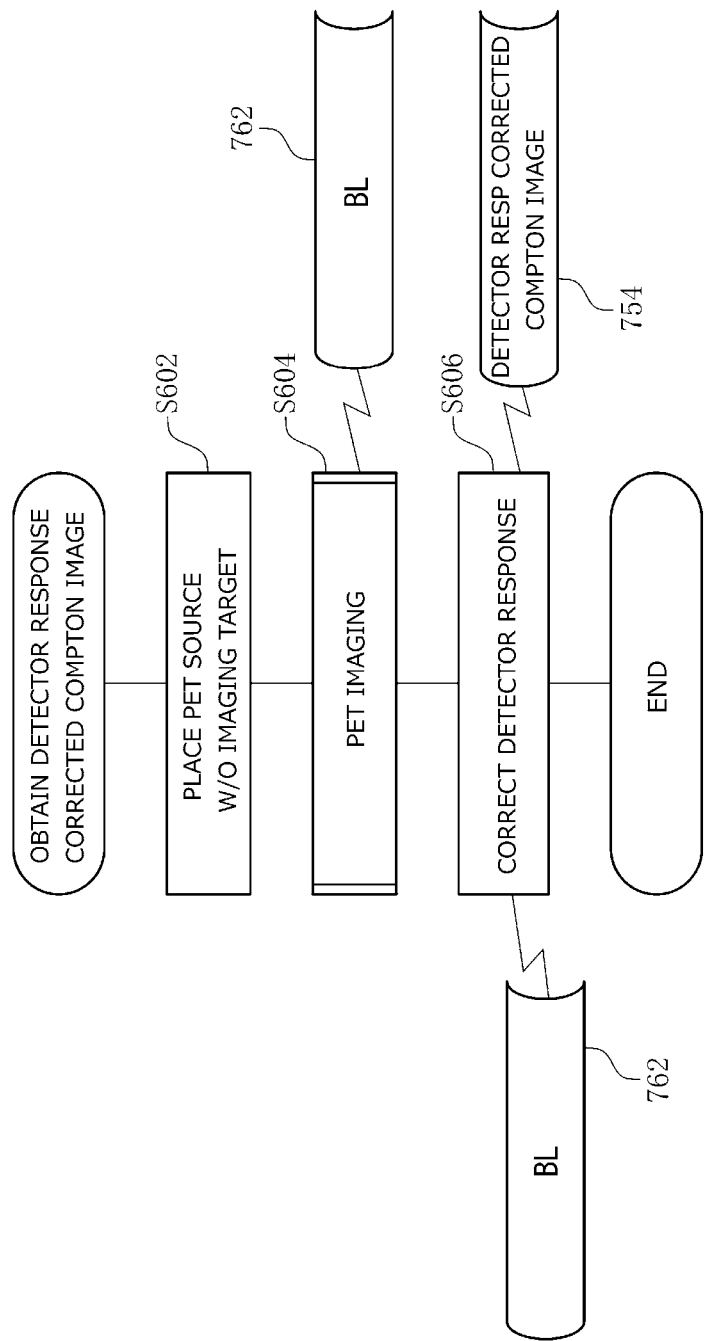
FIG. 14 is a flow chart showing processing for correcting detector response that is used for Compton imaging in an embodiment of the present invention.

FIG. 14 is a flow chart showing processing for correcting detector response for Compton imaging by reflecting blank measurement result of PET imaging. First, a reference radioactive source for PET imaging is placed without placing the imaging target (S602). Thereafter by performing PET imaging (S604) blank PET measurement data is obtained. These processes are performed similarly as in processes S502 and S504 in FIG. 13. Since the obtained blank PET measurement data are values representing efficiency of each point in the detector, they are normalized to have maximum value of 1 for example and stored in the first dose data storage 762 in the computer 690. Note that the steps S602 and S604 can be skipped if the processes S502 and S504 in FIG. 13 were completed and blank PET measurement data have been already stored in the first dose data storage 762.

Next, Compton imaging with placing the imaging target is performed, and the position dependence of the detector efficiency is corrected (S606). This processing is generally the same as one in FIG. 10, and slightly modified to make the correction. The modification is related to the rendering process of the estimated conical surface (S308). More specifically, in the rendering processing of the estimated conical surface, detector efficiency for a point of interaction, or point $P_3$, with the front detector is used. The use of the absorbance is done by dividing values of changes for voxel data by data obtained for the interaction point identical to one of the measured gamma ray out of the blank PET measurement data in the first dose data storage 762. According to this process, a CC SBP image corrected with detector response, or a detector-response-corrected Compton image, is obtained and stored into seventh VDS 754 (S608). The detector-response-corrected Compton image is a corrected result of detector efficiency for Compton scattering to which detector response in PET imaging is reflected.

4-3-3-3. Calibration of Parameters for De-Convolution

As described in Section 4-2, to obtain a high resolution and high accuracy Compton image from a CC SBP image, de-convolution with position dependent PSF for removing effects of position dependency in the response is performed.

Generally speaking, data for determining position dependent PSF may be obtained through the following approaches: (1) actual measurement of a point source, (2) calculation of response by simulation, and (3) determination of position-response function, or position dependent PSF through analytical calculation. Of these approaches (1) and (2) may well be difficult to practice because they need substantial duration for completing through the entire spatial region three-dimensionally. As for (3), the position dependent PSF in Compton imaging should have so complicated profile that it cannot be reproduced by analytical calculation. As a result, it is preferable from a practical point of view that we resort to approximation or estimation that requires some sort of interpolation or extrapolation to have a position dependent PSF with a good accuracy. In so doing, it is also preferable to determine parameters accounting for degree of freedom for the position dependent PSF based on some metrics that are sufficiently reliable. However, since such metrics cannot be usually obtained only through Compton imaging, the true image $^C\lambda_j$ derived through Formulas (6) and (7) is merely a result of calculation based on an assumed position-response function, and thus we need to check the preciseness of the assumed position-response function itself For that purpose, residual $\Delta$ is adopted as an example of preferable metrics, where the residual $\Delta$ is an arbitrary function of difference between the PET image, which is quantitative and high resolution, and the Compton image. Such is adopted because it will be a metrics of similarity between the true image $^C\lambda_j$ of Compton image obtained by de-convolution of the CC SBP image and the true image $^P\lambda_j$ of PET image. In particular, distribution images for an identical probe are captured one through PET imaging and the other Compton imaging, and a position-response function, or position dependent PSF, for de-convolution of Compton imaging is calibrated to minimize the residual $\Delta$ between the two true images for both imaging. This calibration, or optimization of the position dependent PSF, is typically practiced by adjusting parameters that characterize the degree of freedom in position dependence of the position dependent PSF. In so doing, as the residual $\Delta$ to be minimized globally or locally are selected from values that increase when the difference of the PET image and Compton image, both of which are de-convoluted ones, increases. By reflecting the parameters that were adjusted in accordance with the above into the position-response function, it is possible to perform estimation or optimization of the position dependent PSF in such a high accuracy that could never be achieved only with Compton imaging.

Figure 15:
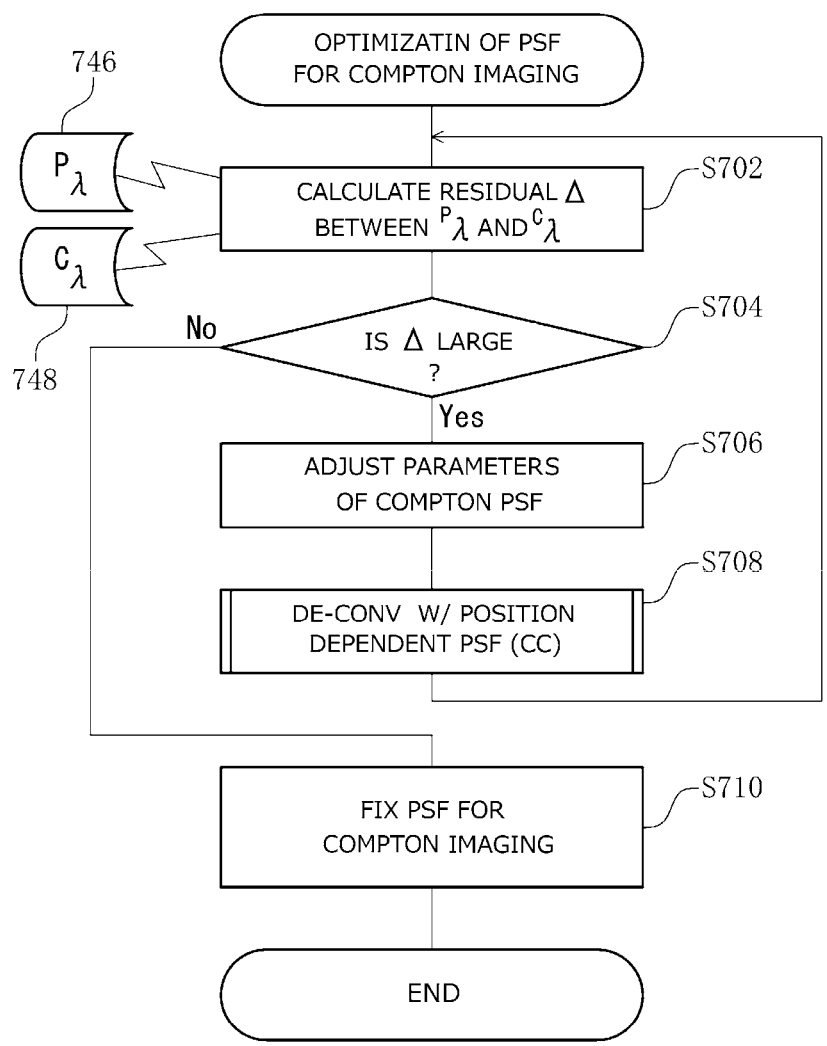
FIG. 15 is a flow chart showing processing for optimization of the position-response function for Compton images using PET images in an embodiment of the present invention.

FIG. 15 is a flow chart showing processing of optimization of the position-response function for Compton images based on PET images. Through the process indicated in FIGS. 11(a) and 11(b) the true images of the Compton image and the PET image were stored in the fourth VDS 748 and the third VDS 746 respectively. These true images are retrieved for computing the residual $\Delta$ (S702). The residual $\Delta$ is calculated from the difference of voxel values in each position, by, such as squared and summed up. As such, a value that indicates the difference of the PET image and Compton image, both of which are de-convoluted, is obtained.

Then the magnitude of the residual $\Delta$ is examined in the determination (S704). When the residual $\Delta$ is large (S704, branch Yes), then parameters for the position-response function for the Compton imaging is changed and adjusted (S706). Next, a process that includes iteration in the Compton imaging is performed again according to FIG. 11(a) while applying the adjusted parameters to the position-response function (S708), and the calculation of residual $\Delta$ and determination are carried out again (S702). When the residual becomes small after the repetition of these steps (S704, branch No), the position-response function to be used in de-convolution for the Compton imaging is fixed (S710). As a result, based on high resolution image obtained by the PET imaging, the position-response function, or the position dependent PSF, for the Compton imaging can be adjusted to lead to higher accuracy.

4-3-3-4. Calibration of Image Position, or Identification of Parts by Comparison In the present embodiment, a Compton image may be aligned using PET measurement data, based on the fact that an identical probe distribution can be captured through PET and Compton camera. The position adjustment is to correct positional shifts between a position in the three-dimensional space to which the Compton image is presented and another position that is an actual position where the imaging target is placed. Generally speaking, image resolution and positional accuracy of a PET image, including PET measurement data, is higher than those of a Compton image. Thus, superimposing the Compton image onto the PET image, or displaying them interchangeably, may enable us to adjust positional shifts with a high accuracy. In particular, one approach is to adjust positions of the Compton and PET images based on visual inspection by an operator who compares Compton and PET images through the superimposition or interchanging presentations on a display device.

To accomplish this position adjustment, necessary steps for changing relative position of Compton image or PET image, including the transmission PET measurement image, may be adopted. For example, changing the translational position, the direction, and the scale for the voxel data for the Compton image, or more generally determining parameters for specifying affine transformation, is used for the process for changing the relative positions between the Compton image and the PET image, including the transmission PET measurement data. In so doing, values for specifying the positional changes are expressed by arbitrary numeric values in a combined values including, offset values for their translational positions, a combination of the rotation angles for their directions, and a magnification scale for the scaling. Therefore, in the values such as the offset value, the rotation angles, and the offsets for the scaling are stored into positional correction data storage 770 (FIG. 7) in association respectively with Compton images stored in the storage. For other approaches than the positional adjustment by the visual inspection, it is possible to use shifts between weights in distributions for an accumulated probe.

It is to be noted that data of PET image applicable to the position adjustment include, but not limited to, a PET SBP image storage in the first VDS 742, a true image of PET image stored in the third VDS 746, and an absorbance-corrected PET image stored in the fifth VDS 750. It is also to be noted that data of Compton image to be aligned includes, but not limited to, a CC SBP image stored in the second VDS 744, a true image of Compton image stored in the fourth VDS 748, an absorbance-corrected Compton image stored in the sixth VDS 752, and a detector-response-corrected Compton image stored in the seventh VDS 754. The positional shifts between PET imaging and Compton imaging may be found typically when the image is captured for the first time, or the image is captured immediately after changing the configuration of semiconductor detectors. In addition, the configuration of semiconductor detectors may be changed, for example, to vary the distances or the directions of the semiconductor detectors in order to fit themselves to the size and the shape of the imaging target.

In addition, when human being or living animal is selected as the imaging target, their internal organ positions differ for each imaging target. Therefore, even though three-dimensional coordinates for positions where the probe is accumulating or accumulated region are measured, it may be unclear which organ or part of the organ is corresponding to the accumulated region in the imaging target of interest. Therefore in the present embodiment it is preferable that, for example, an arbitrary image using a probe that can be captured only by detecting Compton scattering, or the second probe, is superimposed on an arbitrary image captured with a first probe, and thereafter the images are displayed on the display 710 in FIG. 7. The images superimposed are distinguished from each other by such as different colors. If the PET and Compton images are viewed while they are presented at a time or interchanging each other, then we can tell what organ and what parts is accumulated by the second probe having gamma ray emitting nuclei. The PET and Compton images that are displayed distinguishably may include data of various types, similarly to ones in the position adjustment.

4-3-3-5. Determination of Cutoff Frequency

The cutoff frequency for noise filtering applied to Compton imaging may be determined by comparing the images with PET images for the identical target (probe). That is, PET imaging can capture images with better resolution and better S/N ratio than ones in Compton imaging. Therefore, in comparison with the Compton imaging, the PET imaging generates less effects of noise for higher frequency. It follows that, in signal components for the spatial frequency obtained from the identical target, it is easier for the PET imaging than the Compton imaging to determine an upper limit of the spatial frequency below which the data should be retained. Therefore it is preferable that a frequency is determined for a measure of the upper limit of special frequency for the signal component to be retained by, for example, choosing a PET image measured with an identical probe administration as in FIG. 12, and that such frequency is adopted as a cutoff frequency for filtering of Compton imaging. Note that the cutoff frequency determined in this manner may also be applicable to other images than Compton imaging for energy of 511 keV.

5. Simultaneous Imaging on Multi-Tracer

Practicing the simultaneous imaging on multi-tracer in the present embodiment is typically accomplished by two approaches. One is an approach that uses the first probe to produce gamma rays by pair annihilation and the second probe to produce gamma ray by the gamma ray emitting nuclei (5-1). Another approach is to distinguish plural probes only through Compton imaging (5-2). Moreover, such two typical approaches may be combined (5-3) in the present embodiment. It should be noted that the combination of probes to be administered to the imaging target and to be adopted for the simultaneous imaging of multi-tracer is not limited to combinations that satisfy the relationship as described above. For example, probes having different chemical structures, each of which accumulates to an identical part in the living body with different timing may be adopted.

5-1. Simultaneous Imaging on Multi-Tracer with First and Second Probes

In the first typical approach, which uses the first and second probes, PET imaging is performed for gamma rays of pair annihilation originating from the first probe, and Compton imaging for a gamma ray originating from the second probe. Therefore, the captured PET and Compton images are displayed in association respectively with the accumulation regions of the first and second probes. What are displayed as the PET image in association with the accumulation region of the first probe are, for example, the PET SBP image stored in the first VDS 742, the true image of PET image in the third VDS 746, and the absorbance-corrected PET image in the fifth VDS 750. In contrast, what are displayed as the Compton image in association with the accumulation region of the second probe are, for example, the CC SBP image stored in the second VDS 744, the true image of Compton image in the fourth VDS 748, the absorbance-corrected Compton image in the sixth VDS 752, and the detector-response-corrected Compton image in the seventh VDS 754.

For displaying results in the simultaneous imaging on multi-tracer, the display 710 of the computer 690 is utilized. In so doing, voxel data for PET image and Compton image associated with the first and second probe respectively are displayed based on a common coordinate in a manner distinction can be made from each other. Displaying the voxel data in such a manner may be accomplished by an arbitrary approach, such as, by displaying only significant valued parts out of the voxel data with distinguishable colors from each other. In addition, a displaying format presenting the voxel data may be arbitrary one, including any type of two and three-dimensional formats. Examples of the two-dimensional format are various processed images derived from the voxel data, including a cross sectional view, a projection view that is projected onto an arbitrary surface, a perspective view, and a contour image. Additionally it is possible that, in connection with delineation of a region in either two or three dimension, the entire data within the region for each probe in the image are summed up, and that numeric texts or some sort of indications corresponding to the summed values are displayed as numerical values or metrics for each radioactivity.

5-2. Simultaneous Imaging on Multi-Tracer Only by Compton Imaging

The other typical approach is that multi probes are imaged differently by Compton imaging alone. For this purpose, imaging gamma rays with different energy can be imaged differently by administering to the imaging target a plurality types of probes, each of which are labeled with respective type of gamma ray emitting nuclei, as the second probe as mentioned above. When this approach is adopted, a part of process of Compton imaging described in connection with FIG. 10 is modified. That is, for the determination as to whether the full-energy has been absorbed or not (S302), a plurality of mathematical relationships as $E_0=E_1+E_2$, each associated with energy of the different types of gamma ray emitting nuclei, are used respectively. The following processes (S304-S308) are performed respectively for gamma ray energies. Moreover, data to be stored in the second VDS 744 as voxel data are also modified. Typically the data to be stored in the second VDS 744 is logically differentiated in a manner that retrieving by specifying energy of gamma ray can be made in future.

Note that it is useful to make preliminary measurement using PET imaging, such as various measurements as described specifically in Section 4-3, even in the simultaneous imaging on multi-tracer by Compton imaging. This is because when performing simultaneous imaging of multi-tracer in Compton imaging, the preliminary measurement make it possible to identify different probe distributions with high accuracy based on highly accurate images.

5-3. Simultaneous Imaging on Multi-Tracer

Furthermore the present embodiment provides the combination of the two typical approaches as mentioned above. First, a first probe for generating gamma rays by pair annihilation and, as a plurality of probes of the second probe, different probes labeled by respective gamma ray emitting nuclides having different energies each other are administered to an imaging target. Then the accumulation image of the first probe is reconstructed with the PET imaging and the each accumulation region of each probe having gamma ray emitting nuclei are reconstructed with the Compton imaging. The simultaneous imaging on multi-tracer with such a combination is also a part of the present embodiment.

Modification 1 of Embodiment 1

The Embodiment 1 of the present invention can be modified in various ways. For example, positions of probes that originated gamma rays can be estimated, even if the process described in Section "2-2-2. Determination of Hit Pattern" is modified. In this Section a modification in which we can reflect actual phenomenon during the coincidence measurement in the determination of hit pattern will be explained as Modification 1.

In Section of "Determination of Hit Pattern" in the above, a typical process of the simplified processing system as in the FIG. 3 was described based on flowcharts in FIGS. 8 to 10. In the description, the number of detectors relating to the coincidence measurement of interactions with gamma rays was limited as two at the maximum, for the purpose of explaining typical detection mechanism in the present embodiment.

In practice, however, when the first-fourth semiconductor detectors 11-22 in FIGS. 1 and 3 are used in the measurement, for example, three separate detectors or all four detectors may have chance to measure coincidence. In such cases, the detection is not accidental coincidence detection, and thus the distribution of the probe may be imaged. For example, assume that a pair of gamma rays of 511 keV originating from the first probe, or a probe having positron decay nuclei, is emitted and each gamma ray is detected by the first and second Compton cameras 10 and 20. Under this assumption, examples of detectors combination that detect interactions should be noted. The examples include one in which a gamma ray entered into the first Compton camera 10 is scattered by Compton scattering in the first semiconductor detector 11, and thereafter detected with full-energy absorption in the second semiconductor detector 12 to cause photoelectric effect, whereas another gamma ray entered into the second Compton camera 20 is detected by photoelectric effect in the third semiconductor detector 21. In this example, three detectors interact simultaneously with gamma rays. However, this was caused by two gamma rays of pair annihilation, and such gamma rays have been emitted from a living body region over which the first probe distributed, such as the living body region 902 in FIG. 1. Therefore this example is not caused by an accidental coincidence measurement and it is possible to perform imaging of the probe distribution.

The processing steps for performing the imaging in the present embodiment can be modified in various ways in response to the actual station as described above. For example, the determination processing of hit pattern S106 in FIG. 8 can be modified, and it is preferable that it is performed under a scheme of case analysis regarding the number of detectors that detected interactions in coincidence, and combining the scheme with another scheme of case analysis based on energy determination, as necessity. In the specific process in the case analysis, the process is divided into cases according to the number of detectors having measured in coincidence in place of the determination processing of hit pattern S106 of FIG. 8. The cases may be one for two detectors, another for three detectors, and another for four detectors, and so on. After dividing into such cases, it is followed by processes (1)-(3) described below.

(1) In the case the number of detectors in coincidence detection is two, the same determination as the determination processing of hit pattern S106 in FIG. 8 is performed. The rest of the processes are those described with reference to FIGS. 9 and 10.

(2) In the case the number of detectors in coincidence detection is three, the process in FIG. 9, or a process obtaining a PET SBP image, is performed concerning data from two detectors satisfying "LEFT-RIGHT" relationship with each other; and the process in FIG. 10, or a process obtaining a CC SBP image, is performed concerning data from two detectors satisfying "FRONT-REAR" relationship. In this case, two series of process steps in FIGS. 9 and 10 are performed not by either of the two, but both of them independently. Typical example is: two detectors of "LEFT-RIGHT" relationship are the first and third semiconductor detector 11 and 21, and two detectors of "FRONT-REAR" relationship are the first and second semiconductor detectors 11 and 12. In the determination of full-energy absorption S302 (FIG. 10), the value 511 keV is used for the full-energy $E_0$. In addition, energy determination of 511 keV in gamma ray energy determination S202 (FIG. 9) is made for another set of gamma rays. Specifically, of the two detectors in "LEFT-RIGHT" relationship, such as the first semiconductor detector 11 and the third semiconductor detector 21, the determination as to whether the energy is 511 keV or not will not be made for a detector selected concurrently as one of the two detectors of "FRONT-REAR" relationship, such as the first semiconductor detector 11. That is, when the number of detectors detected in coincidence is three in Modification 1, of the two detectors of "LEFT-RIGHT" relationship, the determination whether the energy is 511 keV or not is made only for a counterpart of the detector selected as one of the two detectors of "FRONT-REAR" relationship and is made solely based on the energy from the counterpart detector. For the remaining two detectors, the total energy value is examined as to whether it is 511 keV or not, because they satisfy "FRONT-REAR" relationship each other.

The rest of the process steps are performed as described in Sections "3-1. SBP Image for PET Imaging" and "3-2. SBP Imaging for Compton imaging". For example, processes for determining the interaction points to render estimated straight lines, and reconstructing the PET SBP image (S204 and S206) in FIG. 9, as well as estimating a scattering angle, determining interaction points to render estimated conical surfaces, and reconstructing a CC SBP image (S304-S308) in FIG. 10, are performed independently without substantial changes.

(3) In the case the number of detectors in coincidence detection is four, the following processes are performed. In this case, as similarly in (2) for the case when the coincidence detection was found in three detectors, the process in FIG. 9, or a process obtaining a PET SBP image, is performed for data from two detectors satisfying "LEFT-RIGHT" relationship with each other; and the process in FIG. 10, or a process obtaining a CC SBP image, is performed for data from two detectors satisfying "FRONT-REAR" relationship. Also in this case, two series of process steps in FIGS. 9 and 10 are carried out not by either of the two, but both of them independently. Note that Typical example for two detectors of "LEFT-RIGHT" relationship are the first and third semiconductor detectors 11 and 21, and two detectors that are "FRONT-REAR" relationship are two combinations, of the first and second semiconductor detectors 11 and 12, and of the third and fourth semiconductor detectors 21 and 22. As similarly in case (2), in the determination of full-energy absorption S302 (FIG. 10), 511 keV is used for the full-energy $E_0$. Thus, energy determination of 511 keV in gamma ray energy determination S202 (FIG. 9) is made not for energy from a single detector, but for sum of absorbed energy in two detectors satisfying "FRONT-REAR" with each other. The rest of the processes in FIGS. 9 and 10 are those as described in Sections "3-1. SBP Image for PET Imaging" and "3-2. SBP Image for Compton imaging". In particular, the process in FIG. 10 is repeated two times, because the number of combination of the detectors in "FRONT-REAR" relationship is two.

As described here under Modification 1, even when the number of detectors actually detected interactions with gamma ray in coincidence is two or more, the present embodiment can be practiced with appropriate modifications in consideration of specific conditions for the practice. That is, independent processes in "SBP Image for PET imaging" in Section 3-1 and "SBP Image for Compton imaging" in Section 3-2 are applicable to cases for more than two detectors.

Modification 2 of Embodiment 1

As another modification, Modification 2, of the Embodiment 1 of the present invention description will be made for a case when a scintillation detector is adopted for a part of the first and second Compton cameras 10 and 20. The detectors for the first or second Compton camera 10 or 20 in the present embodiment may include a scintillation detector. The scintillation detector used for a PET imaging device of general kind has a scintillator and a photo detector. Examples of scintillators that can be used in the present modification may include sodium iodide (NaI), cesium iodide (CsI), bismuth germanium oxide (BSO), lanthanum tribromide (LaBr), gadolinium sulfate oxide (GSO), gadolinium oxysulfide (GSO), lutetium oxysulfide (LSO), and so on. The photo detector combined with such scintillator, may include photo multipliers, or an avalanche photo diode (APD) made of semiconductor.

Note that scintillation detectors generally do not have such a high energy resolution as the semiconductor detectors. However, since the energy of the emitted gamma ray in particular for Compton scattering is already known, thus, if the energy is determined by one of the front and rear detector, then the energy for the other of them will be uniquely derived. It follows that the energy resolution of scintillation detectors is acceptable as long as it is used as either of the front or rear detector. For example, the present embodiment may be practiced with a Compton camera having a semiconductor detector as one of the front and the rear detectors, and a scintillation detector as the other of them. In such a case, an energy value according to a detector having higher energy resolution out of the front and rear detectors may be used in analyzing the kinematics of the Compton scattering for obtaining satisfactory accuracy in the scattering angle $\theta$ as described with reference to Formula (1).

Moreover, also in Compton cameras in the ring arrangement as described in "1. Detectors Configuration" of the present embodiment, or in Compton cameras having existing PET imaging device and additional semiconductor detectors, the existing scintillation detector may be used for a detector corresponding to the front or rear detector. For example, in addition to the existing PET imaging device equipped with the scintillation detectors in a ring arrangement, placing semiconductor detectors outside of the ring of the scintillation detectors may be adopted for the present modification. In this structure the capability of simultaneous imaging on multi-tracer capability utilizing the Compton scattering is added to one for the existing PET imaging device, because the scintillation detector plays a role of the front detector in Compton camera, and the semiconductor detector plays a role of the rear detector.

The embodiment of the present invention has been described specifically throughout the above description. Any description in this Specification is for the purpose of explaining the present invention, therefore the scope of the invention should be determined based on recitations of the claims. Furthermore, other variation based on any combination of the embodiment is included in the present invention, which variation should be also within a scope of the present invention.

INDUSTRIAL APPLICABILITY

According to the present invention, the PET image and the Compton image are captured by an identical piece of equipment. Thus the present invention contributes to realization of simultaneous imaging of multi-tracer with improved accuracy, and practicing diagnostic device for nuclear medicine or research instrument of tracer imaging.

| Reference Signs List | |
| --- | --- |
| 100 | gamma ray imaging device |
| 10, 20 | first and second Compton cameras |
| 900, 950 | imaging target |
| 902, 904, 952 | living body region |
| 11 | first semiconductor detector (front detector) |
| 12 | second semiconductor detector (rear detector) |
| 21 | third semiconductor detector (front detector) |
| 22 | fourth semiconductor detector (rear detector) |

-continued

| Reference Signs List | |
|---|---|
| 24, 25 | gamma ray |
| 24C, 25C | conical surface |
| 32, 34 | coincidence finder |
| 36, 38 | imaging processor |
| 40 | circuit structure |
| 402 | pre-amplifier (Pre-AMP) |
| 404 | timing filtering amplifier (TFA) |
| 406 | constant fraction discriminator (CFD) |
| 408 | shaping amplifier (S-AMP) |
| 410, 414A, 414B, 420 | OR gate |
| 412 | delay circuit |
| 416A, 416B, 418 | AND gate |
| 422 | Gate&Delay |
| 470 | time-to-digital converter (TDC) |
| 480 | analog-to-digital converter (ADC) |
| 490, 690 | computer |
| 492-498 | first-the fourth event data storages |
| 50 | coincidence measurement finder |
| 52-58 | first-fourth measurement signal channels |
| 60 | signal channel |
| 602 | pre-amplifier |
| 604 | amplifier (AMP) |
| 606 | ADC |
| 608 | digital signal processor (DSP) |
| 610 | clock generator |
| 612 | energy field |
| 614 | time field |
| 616 | data buffer |
| 702 | bus |
| 704 | microprocessor unit (MPU) |
| 706 | memory (MEM) |
| 708 | input/output (I/O) |
| 710 | display |
| 712 | mouse |
| 714 | keyboard |
| 720 | storage |
| 722-728 | first-fourth measurement data storage (MDS) |
| 742 | first voxel data storage (VDS) (PET SBP image) |
| 744 | second voxel data storage (CC SBP image) |
| 746 | third voxel data storage (true image of PET image) |
| 748 | fourth voxel data storage (true image of Compton image) |
| 750 | fifth voxel data storage (absorbance (ρ)-corrected PET image) |
| 752 | sixth voxel data storage (absorbance (ρ)-corrected Compton image) |
| 754 | seventh voxel data storage (detector-response-corrected Compton image) |
| 762 | first dose data storage (blank PET measurement data) |
| 764 | second dose data storage (transmission PET measurement data) |
| 766 | third dose data storage (gamma ray absorbance data, ρ) |
| 770 | positional correction data storage |

What is claimed is:

1. An imaging device using gamma rays comprising:
a first Compton camera adapted to receive one gamma ray emitted from an imaging target to which a first probe having positron emitting nuclei and a second probe having gamma ray emitting nuclei are administered;
a second Compton camera arranged opposite to the first Compton camera and adapted to receive another gamma ray emitted from the imaging target;
an imaging processor to perform either a PET image reconstruction or a Compton image reconstruction depending on whether interactions with gamma rays have been detected by the first and the second Compton cameras or interactions with a gamma ray has been detected by either the first or the second Compton camera; and
a display for displaying the PET image and the Compton image in association respectively with an accumulation region of the first probe and an accumulation region of the second probe, in a manner distinction can be made from each other.

2. The imaging device according to claim 1, wherein the first Compton camera has a first semiconductor detector disposed facing the imaging target and a second semiconductor detector disposed behind the first semiconductor detector when viewed from the imaging target, and wherein the one gamma ray is detectable by either the first semiconductor detector or the second semiconductor detector, and
wherein the second Compton camera has a third semiconductor detector disposed facing the imaging target and a fourth semiconductor detector disposed behind the third semiconductor detector when viewed from the imaging target, and wherein the other gamma ray is detectable by either the third semiconductor detector or the fourth semiconductor detector.

3. The imaging device according to claim 2, wherein the first, the second, the third and the fourth semiconductor detectors are multiple electrode planer semiconductor detectors.

4. The imaging device according to claim 2, wherein the first, the second, the third and the fourth semiconductor detectors have medium selected from the group consisting of germanium, silicon, cadmium telluride, cadmium zinc telluride, and diamond.

5. The imaging device according to claim 1, wherein the first Compton camera has a first gamma ray detector disposed facing the imaging target and a second gamma ray detector disposed behind the first gamma ray detector when viewed from the imaging target, wherein the one gamma ray is detectable by either the first or the second gamma ray detector, and wherein one of the first and the second gamma ray detectors is a semiconductor detector and the other of the first and the second gamma ray detectors is a scintillation detector, and
wherein the second Compton camera has a third gamma ray detector disposed facing the imaging target, and a fourth gamma ray detector disposed behind the third gamma ray detector when viewed from the imaging target, wherein the other gamma ray is detectable by either the third or the fourth gamma ray detector, and wherein one of the third and the fourth gamma ray detectors is a semiconductor detector and the other of the third and the fourth gamma ray detectors is a scintillation detector.

6. An image signal processor using gamma rays comprising:
a first reception channel from a first Compton camera, the first Compton camera being adapted to receive one gamma ray emitted from an imaging target to which a first probe having positron emitting nuclei and a second probe having gamma ray emitting nuclei are administered;
a second reception channel from a second Compton camera, the second Compton camera being arranged opposite to the first Compton camera and being adapted to receive another gamma ray emitted from the imaging target;
a coincidence finder connected to both the first and the second reception channels, wherein the coincidence finder determines coincidence detection of gamma rays emitted from the imaging target;
an imaging processor that performs either a PET image reconstruction or a Compton image reconstruction depending on whether the coincidence finder has determined that interactions with gamma rays were detected by the first and the second Compton cameras or that interactions with a gamma ray were detected by either the first or the second Compton camera; and
a display that displays the PET image and the Compton image in association respectively with an accumulation region of the first probe and an accumulation region of the second probe, in a manner distinction can be made from each other.

7. The image signal processor according to claim 6,
wherein the first reception channel has at least a first measurement signal channel that is adapted to transmit a first measurement signal created by a first detector, the first detector being disposed facing the imaging target, and at least a second measurement signal channel that is adapted to transmit a second measurement signal created by a second detector, the second detector being disposed behind the first detector when viewed from the imaging target,
wherein the second reception channel has at least a third measurement signal channel that is adapted to transmit a third measurement signal created by a third detector, the third detector being disposed facing the imaging target and opposite to the first detector, and at least a fourth measurement signal channel that is adapted to transmit a fourth measurement signal created by a fourth detector, the fourth detector being disposed behind the third detector when viewed from the imaging target, and
wherein:
the first Compton camera has the first and the second detectors,
the second Compton camera has the third and the fourth detectors, and
the coincidence finder
outputs a PET determination signal indicating that PET imaging process is to be performed, in response to coincidence detection between a detection signal from either the first or the second detector and another detection signal from either the third or the fourth detector, and
outputs a Compton scattering determination signal indicating that Compton imaging process is to be performed, in response either to coincidence detection between signals from the first and the second detectors or to coincidence detection between signals from the third and the fourth detectors.

8. The image signal processor according to claim 7, further comprising:
a first event data storage for storing data that represents coincidence detection of events in the first measurement signal;
a second event data storage for storing data that represents coincidence detection of events in the second measurement signal;
a third event data storage for storing data that represents coincidence detection of events in the third measurement signal; and
a fourth event data storage for storing data that represents coincidence detection of events in the fourth measurement signal; and
wherein:
the imaging processor reconstructs spatial distribution of the first probe having the positron emitting nuclei by using a straight line connecting two detection points at each of which a gamma ray was detected, based upon data associated with the fact that the PET determination signal has been output out of data in the first-fourth event data storages, and
the imaging processor reconstructs spatial distribution of the second probe having the gamma ray emission nuclei by using a cone, wherein the cone has either a straight line connecting two interaction points of a gamma ray in the first and the second detectors or a straight line connecting two interaction points of a gamma ray in the third and the fourth detectors as its axis, an interaction point of the gamma ray in either the first or the third detector as its apex, and a scattering angle that is determined according to kinematics of the Compton scattering as its half-angle at the apex.

9. An image processing method for gamma ray measurement data, causing a processor in a computer to perform the method, the method comprising steps of:
storing measurement data to a storage in a computer, the measurement data obtained by a first Compton camera that is adapted to receive one gamma ray emitted from an imaging target to which a first probe having positron emitting nuclei and a second probe having gamma ray emitting nuclei are administered and obtained by a second Compton camera that is arranged opposite to the first Compton camera and is adapted to receive another gamma ray emitted from the imaging target;
coincidence finding for finding coincidence regarding a gamma ray emitted from the imaging target based on the measurement data stored in the storage;
imaging processing for performing either PET image reconstruction or Compton image reconstruction depending on whether interactions with gamma rays have been detected by the first and the second Compton cameras or interactions with a gamma ray have been detected by either the first or the second Compton camera; and
displaying the PET image and the Compton image in association respectively with an accumulation region of the first probe and an accumulation region of the second probe, in a manner distinction can be made from each other.

10. The image processing method according to claim 9, wherein the step of storing measurement data to the storage includes steps of:
receiving a first measurement data from a first detector in the first Compton camera, the first detector disposed facing the imaging target, and storing the first measurement data in association with time stamp data from a clock signal to a first measurement data storage in the computer;
receiving a second measurement data from a second detector in the first Compton camera, the second detector being disposed behind the first semiconductor detector when viewed from the imaging target, and storing the second measurement data in association with time stamp data from the clock signal to a second measurement data storage in the computer;
receiving a third measurement data from a third detector in the second Compton camera, the third detector being arranged opposite to the first detector with the imaging target in between, and storing the third measurement data in association with time stamp data from the clock signal to a third measurement data storage in the computer; and
receiving a fourth measurement data from a fourth detector in the second Compton camera, the fourth detector being disposed behind the third semiconductor detector when viewed from the imaging target, and storing the fourth measurement data in association with time stamp data from the clock signal to a fourth measurement data storage in the computer, wherein the coincidence finding step includes steps of:
selecting, from the first-fourth measurement data retrieved from the first-fourth measurement data storages, at least two values that have respective time stamp data falling within a predetermined allowable time difference and were obtained by different detectors;

comparing measurement data in the first-fourth measurement data by correlating one another based on the time stamp data;

generating a PET determination signal when detections between either of the first or the second measurement data and either of the third or the fourth measurement data are found within the predetermined allowable time difference, the PET determination signal indicating that PET imaging process is to be performed for each measurement data; and generating a Compton scattering determination signal when detections in the first and the second measurement data are found within the predetermined allowable time difference, or when detections in the third and the fourth measurement data are found within the predetermined allowable time difference, the Compton scattering determination signal indicating that Compton imaging process is to be performed for each measurement data, wherein the imaging processing step is to reconstruct the PET image or the Compton image depending on whether the signal generated in the coincidence finding step was the PET determination signal or the Compton scattering determination signal.

11. The image processing method according to claim 9, wherein the imaging processing step includes a step of determining energy values for determining whether both of measurement data from the first Compton camera and measurement data from the second Compton camera indicate an energy value of 511 keV.

12. The image processing method according to claim 10, wherein the imaging processing step includes steps of:
determining interaction points, when the PET determination signal is generated by the processor, for determining a first interaction point that is an interaction point of the one gamma ray in either the first detector or the second detector, and a second interaction point of the other gamma ray in either the third detector or the fourth detector; and straight line rendering by changing values of voxels in a first voxel data storage in the computer, the voxels corresponding to a straight line connecting the first interaction point and the second interaction point.

13. The image processing method according to claim 10, wherein the imaging processing step includes a step of determining an energy value, when the Compton scattering determination signal is generated by the processor, for determining whether at least one of or both of a sum value of energies respectively indicated by the first and the second measurement data and a sum value of energies respectively indicated by the third and the fourth measurement data indicate an energy value of a gamma ray emitted from gamma ray emission nuclei in the second probe or not.

14. The image processing method according to claim 13, wherein the imaging processing step includes steps of:
determining interaction points, when the Compton scattering determination signal is generated by the processor, for causing the processor to determine a third interaction point that is an interaction point of Compton scattering by a gamma ray in either the first detector or the third detector, and a fourth interaction point of the gamma ray after the Compton scattering in either the second detector or the fourth detector;

computing a scattering angle of the Compton scattering in either the first detector or in the third detector, by applying an energy value indicated in the first or the third measurement data and an energy value indicated in the second and the fourth measurement data to kinematics of Compton scattering; and conical surface rendering by changing values of voxels in a second voxel data storage in the computer, the voxels corresponding to a surface of a cone, wherein the cone has a straight line connecting the third and the fourth interaction points as its axis, the third interaction point as its apex, and the scattering angle as its half-angle at the apex.

15. The image processing method according to claim 14, wherein the imaging processing step includes a step of operating iteration for generating through iteration a de-convoluted Compton image after the conical surface rendering step in accordance with a following recurrence equation for images retrieved from the second voxel data storage,

[Formula 1]

$$\begin{cases} {}^C\lambda_j^{(0)} = \frac{1}{N}\sum_{i=1}^{N} {}^C n_i \\ {}^C\lambda_j^{(m+1)} = {}^C\lambda_j^{(m)} + \sum_i \left({}^C n_i - \sum_k {}^C\lambda_k^{(m)}\, {}^C p_{ik}\right){}^C p_{ij} \end{cases},$$

where m is an integer number greater than or equal to 0, ${}^C n_i$ is a voxel value of index i indicating a position in a Compton image retrieved from the second voxel data storage, ${}^C p_{ij}$ is a position-response function for Compton images, the position-response function depending on its position and indicating contributions of spread from a position indicated by index j ("position j") to position i, and ${}^C\lambda_j^{(m)}$ is a sequence representing voxel values ${}^C\lambda_j$ at position j for a true image of the Compton image.

16. The image processing method according to claim 12, wherein the imaging processing step includes a step of operating iteration for generating through iteration a de-convoluted PET image after the straight line rendering step in accordance with a following recurrence equation for images retrieved from the first voxel data storage,

[Formula 2]

$$\begin{cases} {}^P\lambda_j^{(0)} = \frac{1}{N}\sum_{i=1}^{N} {}^P n_i \\ {}^P\lambda_j^{(m+1)} = {}^P\lambda_j^{(m)} + \sum_i \left({}^P n_i - \sum_k {}^P\lambda_k^{(m)}\, {}^P p_{ik}\right){}^P p_{ij} \end{cases},$$

where m is an integer number greater than or equal to 0, ${}^P n_i$ is a voxel value of index i indicating a position in a PET image retrieved from the first voxel data storage, ${}^P p_{ij}$ is a position-response function for PET images, the position-response function depending on its position and indicating contributions of spread from a position indicated by index j ("position j") to position i, and $^P\lambda_j^{(m)}$ is a sequence representing voxel values $^P\lambda_j$ at position j for a true image of the PET image.

17. The image processing method according to claim 14, causing a computer to perform the method, further comprising steps of:

measuring PET measurement data for obtaining blank PET measurement data by performing PET imaging without placing an imaging target at a position between the first and the third detectors but rather with placing a reference radiation source for PET imaging that includes positron emitting nuclei leading to pair annihilation, and storing the blank PET measurement data to a first radiation source data storage in the computer;

transmission measurement for obtaining a transmission PET measurement data by performing PET imaging with placing the reference radiation source for PET imaging at a position outside of an imaging target and between the first and the third detectors, and storing the transmission PET measurement data to a second radiation data storage in the computer; and computing absorbance for obtaining gamma ray absorbance at points in the imaging target by subtracting values of the transmission PET measurement data retrieved from the second radiation data storage from values of the blank PET measurement data retrieved from the first radiation data storage, and wherein the conical surface rendering step includes a step of Compton image absorbance correction for adjusting, when changing voxel values corresponding to the surface of the cone, amounts of changes in voxel values corresponding to the surface of the cone in the second voxel data storage in the computer, after retrieving, from the third radiation data storage, gamma ray absorbance of the imaging target for detection directions that lie on generatrixes of the cone.

18. The image processing method according to claim 15, wherein the imaging processing step includes steps of:

determining interaction points, when the PET determination signal is generated by the processor, for determining a first interaction point that is an interaction point of the one gamma ray in either the first detector or the second detector, and a second interaction point of the other gamma ray in either the third detector or the fourth detector;

straight line rendering by changing values of voxels in a first voxel data storage in the computer, the voxels corresponding to a straight line connecting the first interaction point and the second interaction point;

operating iteration for generating through iteration a de-convoluted PET image after the straight line rendering step in accordance with a following recurrence formula for images retrieved from the first voxel data storage,

[Formula 3]

$$\begin{cases} ^P\lambda_j^{(0)} = \frac{1}{N}\sum_{i=1}^{N} {^Pn_i} \\ ^P\lambda_j^{(m+1)} = {^P\lambda_j^{(m)}} + \sum_i \left( {^Pn_i} - \sum_k {^P\lambda_k^{(m)}} {^Pp_{ik}} \right) {^Pp_{ij}} \end{cases}$$

where m is an integer number greater than or equal to 0, $^Pn_i$ is a voxel value of index i indicating a point in a PET image retrieved from the first voxel data storage, $^Pp_{ij}$ is a position-response function for PET images, the position-response function depending on its position and indicating contributions of spread from a position indicated by index j ("position j") to position i, and $^P\lambda_j^{(m)}$ is a sequence representing voxel values $^P\lambda_j$ of position j for a true image of the PET image;

operation step for computing values representing difference between the de-convoluted PET image and the Compton image; and position dependent PSF estimation step by changing parameters for the position-response function for Compton images in such a way that the difference is decreased.

19. The image processing method according to claim 14, wherein the imaging processing step includes steps of:

determining interaction points, when the PET determination signal is generated by the processor, for determining a first interaction point that is an interaction point of the one gamma ray in either the first detector or the second detector, and a second interaction point of the other gamma ray in either the third detector or the fourth detector;

straight line rendering by changing values of voxels in a first voxel data storage in the computer, the voxels corresponding to a straight line connecting the first interaction point and the second interaction point; and storing data to a positional correction data storage in the computer, wherein the data represent positional shifts among accumulation regions of the same type of probes in data of captured data from which PET imaging has been performed or of a PET image derived, and in data of captured data from which Compton imaging has been performed or of a Compton image derived.

* * * * *